United States Patent
Krueger

(10) Patent No.: US 9,168,395 B2
(45) Date of Patent: *Oct. 27, 2015

(54) HAIR CARE PRODUCTS WITH SELECTED AMINO FUNCTIONAL SILICONES AND CATIONIC KERATIN

(71) Applicant: Henkel AG & Co. KGaA, Duesseldorf (DE)

(72) Inventor: Marcus Krueger, Ellerhoop (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,279

(22) Filed: Oct. 25, 2013

(65) Prior Publication Data

US 2014/0116458 A1    May 1, 2014

(30) Foreign Application Priority Data

Oct. 25, 2012  (DE) .......................... 10 2012 219 583

(51) Int. Cl.
*A61Q 5/12* (2006.01)
*A61Q 5/00* (2006.01)
*A61K 8/65* (2006.01)
*A61K 8/898* (2006.01)

(52) U.S. Cl.
CPC ... *A61Q 5/12* (2013.01); *A61K 8/65* (2013.01); *A61K 8/898* (2013.01); *A61Q 5/002* (2013.01); *A61Q 5/004* (2013.01); *A61Q 5/006* (2013.01)

(58) Field of Classification Search
None
See application file for complete search history.

(56) References Cited

U.S. PATENT DOCUMENTS

| | | | |
|---|---|---|---|
| 6,451,300 B1 * | 9/2002 | Dunlop et al. | 424/70.27 |
| 8,740,995 B1 * | 6/2014 | Schweinsberg et al. | 8/405 |
| 8,778,032 B2 * | 7/2014 | Schweinsberg et al. | 8/405 |
| 8,784,507 B2 * | 7/2014 | Schweinsberg et al. | 8/405 |
| 8,790,417 B2 * | 7/2014 | Schweinsberg et al. | 8/405 |
| 8,814,952 B2 * | 8/2014 | Schweinsberg et al. | 8/405 |
| 8,894,984 B2 * | 11/2014 | Schulze Zur Wiesche et al. | 424/70.122 |
| 8,900,329 B2 * | 12/2014 | Schulze Zur Wiesche et al. | 8/405 |
| 8,900,561 B2 * | 12/2014 | Schulze Zur Wiesche | 424/70.122 |
| 2009/0041706 A1 * | 2/2009 | Molenda et al. | 424/70.9 |

OTHER PUBLICATIONS

V Croda Raw Materials, Speciallity ingredients for personal care, Nov. 2005, Croda Chemicals Europe Ltd.*

* cited by examiner

*Primary Examiner* — Jyothsna Venkat
(74) *Attorney, Agent, or Firm* — David K. Benson

(57) ABSTRACT

Hair treatment agents include selected aminofunctional silicones and a selected cationic keratin hydrolysate.

7 Claims, No Drawings

HAIR CARE PRODUCTS WITH SELECTED AMINO FUNCTIONAL SILICONES AND CATIONIC KERATIN

FIELD OF THE INVENTION

The present invention generally relates to hair treatment agents containing selected aminofunctional silicones and a selected cationic keratin hydrolysate.

BACKGROUND OF THE INVENTION

A need exists to further improve hair care products and to impart further advantageous properties to them. In particular, a care-providing complex should be made available that ideally can be used even in conjunction with oxidizing agents and surfactant agents.

Environmental influences and oxidative hair treatments often result in degraded combability properties of the dry and the wet hair. In addition, the shine and moisture balance are disadvantageously influenced by the fact that the external structure of the keratinic fibers has been attacked. A further consequence of repeated treatments of keratinic fibers using surfactant agents and/or oxidizing agents is considerable grease re-absorption by the keratinic fibers, as well as a strong tendency to increased formation of scalp dandruff.

It is therefore an object of the present invention to decrease the side-effects of environmentally related influences and of oxidative as well as surfactant hair treatments, preferably already during the oxidative or surfactant hair treatment but also after the oxidative or surfactant hair treatment, without degrading the efficiency of oxidative or surfactant cosmetic substances, in particular with regard to color intensity, color fidelity, lightening performance or waving effect, and to prevent grease re-absorption by the keratinic fibers and increased formation of scalp dandruff. In addition, the oxidative treatment of keratin-containing fibers, in particular human hair, is also to be combined in the form of a 2-in-1 product, in one application step, with the application of effective fiber protection from environmental influences, for example UV protection.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic composition containing, in a suitable cosmetic carrier, based in each case on the total weight of the composition: a) at least one selected aminofunctional silicone, in a total quantity from 0.01 to 10.0 wt %; b) at least one selected cationic keratin hydrolysate, in a total quantity from 0.1 to 10.0 wt %.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that the object of the present invention can be achieved to an outstanding extent by means of a hair treatment agent that contains an active substance complex containing as essential ingredients at least one selected aminofunctional silicone compound and a selected cationic vegetable surfactant.

Hair treatment agents containing this active substance complex result in improved avivage, improved shine, improved moisture balance, and protection from oxidative damage, and in prevention of grease re-absorption by the keratinic fibers and in an increase in the washing fastness of colored keratinic fibers, in particular of human hair, and in a time delay in the formation of dandruff. A first subject of the present invention is therefore a hair treatment agent containing, in a suitable cosmetic carrier, based in each case on the total composition of the agent:

a) at least one selected aminofunctional silicone, in a total quantity from 0.01 to 10.0 wt %,
b) at least one selected cationic keratin hydrolysate, in a total quantity from 0.01 to 10.0 wt %.

The use of this combination results in surprisingly good properties of the treated hair, in particular improved combability, improved shine, and improved elasticity as well as appreciably enhanced washing fastness for colored hair, and to greater durability simultaneously with better reshaping performance in the context of waving operations such as water waving and permanent waving.

"Hair treatment agents" for purposes of the present invention are, for example, hair shampoos, hair conditioners, conditioning shampoos, hair rinses, hair treatments, hair packs, hair tonics, hair coloring shampoos, or combinations thereof. Compositions that condition the hair, such as hair rinses, hair treatments, hair packs, hair oils and lotions, both as leave-on products, i.e. ones that remain on the hair until the hair is next washed, and as rinse-off products, i.e. products to be rinsed off again a few seconds to a few hours after utilization, are to be understood in particular as hair treatment agents according to the present invention.

"Combability" is understood according to the present invention as both the combability of the wet fibers and the combability of the dry fibers.

"Softness" is defined as the tactility of an assemblage of fibers, in which context one skilled in the art sensorially feels and evaluates the "fullness" and "suppleness" parameters of the assemblage.

"Shapability" is understood as the ability to impart a change in shape to an assemblage of previously treated keratin-containing fibers, in particular human hairs. The term "stylability" is also used in hair cosmetics.

"Restructuring" is to be understood for purposes of the invention as a reduction in the damage to keratinic fibers resulting from a wide variety of influences. Restoration of natural strength plays an essential role here, for example. Restructured fibers are notable for improved shine, improved softness, and easier combability. In addition, they exhibit improved strength and elasticity. Successful restructuring can moreover be demonstrated physically as an increase in melting point as compared with the damaged fiber. The higher the melting point of the hair, the stronger the structure of the fiber.

"Washing fastness" is to be understood for purposes of the invention as maintenance of the original coloring, in terms of shade and/or intensity, when the keratinic fiber is exposed to the repeated influence of aqueous agents, in particular surfactant-containing agents such as shampoos.

The compositions according to the present invention containing the active substance complex according to the present invention are further notable for an appreciably improved state of the keratinic fibers in terms of the moisture balance of the keratinic fibers. The active substance complex according to the present invention furthermore results in appreciable protection of the keratinic fibers from heat effects, for example when blow-drying keratinic fibers. Protection of the surface of keratinic fibers from heat effects is of great importance in particular when irons or hair driers are used. Lastly, it has been found, surprisingly, that the compositions according to the present invention result in appreciably delayed re-soiling of the keratinic fibers.

An aqueous cosmetic carrier contains at least 50 wt % water.

"Aqueous alcoholic" cosmetic carriers are to be understood for purposes of the present invention as aqueous solutions containing 3 to 70 wt % of a $C_1$ to $C_6$ alcohol, in particular methanol, ethanol, propanol, isopropanol, butanol, isobutanol, tert-butanol, n-pentanol, isopentanols, n-hexanol, isohexanols, glycol, glycerol, 1,2-pentanediol, 1,5-pentanediol, 1,2-hexanediol, or 1,6-hexanediol. The agents according to the present invention can additionally contain further organic solvents such as, for example, methoxybutanol, benzyl alcohol, ethyl diglycol, or 1,2-propylene glycol. All water-soluble organic solvents are preferred in this context. Water is particularly preferred.

The first ingredient a) according to the present invention is at least one selected aminofunctional silicone. Aminofunctional silicones are ingredients in cosmetic preparations which have been known and used successfully for some time. From the plurality of aminofunctional silicones, the following aminofunctional silicones are best suited in the active substance combination according to the present invention for achieving the effects according to the present invention.

Suitable diquaternary silicones are selected from compounds of the general formula (Si3c)

$$[R^1R^2R^3N^+\text{-}A\text{-}SiR^7R^8\text{---}](O\text{---}SiR^9R^{10})_n\text{---}O\text{---}SiR^{11}R^{12}\text{-}A\text{-}N^+R^4R^5R^6]\ 2X^- \quad \text{(Si3c)}$$

where residues R1 to R6 mutually independently signify C1 to C22 alkyl residues that can contain hydroxy groups, and where by preference at least one of the residues comprises at least 8 carbon atoms and the remaining residues comprise 1 to 4 carbon atoms, residues R7 to R12 mutually independently are identical or different and signify C1 to C10 alkyl or phenyl, A signifies a divalent organic connecting group, n is a number from 0 to 200, by preference from 10 to 120, particularly preferably from 10 to 40, and $X^-$ is an anion.

The divalent connecting group is by preference a C1 to C12 alkylene or alkoxyalkylene group that can be substituted with one or more hydroxyl groups.

Particularly preferably, the group is —(CH$_2$)$_3$—O—CH$_2$—CH(OH)—CH$_2$—.

The anion $X^-$ can be a halide ion, an acetate, an organic carboxylate, or a compound of the general formula $RSO_3^-$, in which R has the meaning of C1 to C4 alkyl residues.

Preferred diquaternary silicones have the general formula (Si3d)

$$[RN^+Me_2\text{-}A\text{-}(SiMe_2O)_n\text{---}SiMe_2\text{-}A\text{-}N^+Me_2R]$$
$$2CH_3COO^- \quad \text{(Si3d),}$$

in which A is the group —(CH$_2$)$_3$—O—CH$_2$—CH(OH)—CH$_2$—,

R is an alkyl residue having at least 8 carbon atoms, and n is a number from 10 to 120.

Suitable silicone polymers having two terminal quaternary ammonium groups are known by, the INCI name Quaternium-80. These are dimethylsiloxanes having two terminal trialkylammonium groups. Diquaternary polydimethylsiloxanes of this kind are marketed by the Evonik company under the commercial names Abil® Quat 3270, 3272, and 3474.

Hair treatment agents preferred according to the present invention are characterized in that they contain, based on their weight, 0.01 to 10 wt %, by preference 0.01 to 8 wt %, particularly preferably 0.1 to 7.5 wt %, and in particular 0.2 to 5 wt % aminofunctional silicone(s) and/or diquaternary silicone.

Further cationic aminosilicones having at least three terminal aminofunctional groups have only recently been offered commercially. These cationic silicone polymers are notable for the fact that they comprise a silicone skeleton as well as optionally a polyether part and furthermore at least one part having an ammonium structure. Examples of preferred cationic silicone polymers for purposes of the present invention are in particular the compounds having the INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, as well as Silicone Quaternium-2 Panthenol Succinate and Silicone Quaternium-16/Glycidyl Dimethicone Crosspolymer. Silicone Quaternium-22 is, in particular, most preferred. This raw material is marketed, for example, by the Evonik company under the commercial name Abil® T-Quat 60.

Aminofunctional silicones having morpholino groups in the molecule have become available only recently. They optimize the properties of the composition according to the present invention in outstanding fashion. At least one 4-morpholinomethyl-substituted silicone of formula (V) is therefore very particularly preferably used as an aminofunctional silicone:

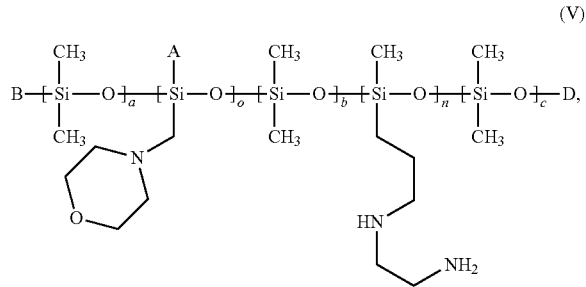

(V)

in which
A denotes a structural unit (I), (II), or (III) bound via —O—

(I)

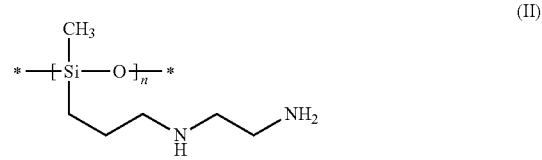

(II)

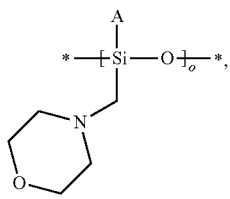

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name Amodimethicone/Morpholinomethyl Silsesquioxane Copolymer. A particularly suitable amodimethicone is the product having the commercial name Wacker Belsil® ADM 8301E.

It can be particularly advantageous according to the present invention if exclusively the silicones recited above are used as silicones. The aforementioned cationic aminofunctional silicones are contained in the compositions according to the present invention in quantities from 0.01 to 10 wt %, preferably in quantities from 0.05 to 7.5 wt %, and very particularly preferably in quantities from 0.1 to 7.5 wt %. The best results of all are obtained with quantities from 0.1 to 5 wt %, based on each case on the total composition of the respective agent.

The second obligatory component of the active substance complex is at least one cationic keratin hydrolysate of formula (I)

in which

R' denotes a straight-chain or branched, saturated or unsaturated hydrocarbon residue having 11 to 24 carbon atoms, R" signifies a protein, a peptide, or a protein hydrolysate, X denotes —C(O)O— or —N$^+$R$^{III}_2$R$^{IV}$— or —N(R$^{III}$)R$^{IV}$— or —C(O)—N(R$^V$)R$^{VI}$—, R$^{III}$ signifies —(CH$_2$)$_x$—CH$_3$ where x=0 to 22, and R$^{IV}$ signifies —CH$_2$—CH(OH)—CH$_2$— or —(CH$_2$)$_x$— where x=0 to 22, R$^V$ and R$^{VI}$ mutually independently denote —H or —(CH$_2$)$_x$—CH$_3$ where x=0 to 22, with the provision that R" denotes keratin or a keratin hydrolysate.

Highly preferably, residue R' denotes a lauryl group and X denotes —N$^+$R$^{III}_2$R$^{IV}$—, where particularly preferably R$^{III}$ denotes —CH$_3$ and R$^{IV}$ denotes —CH$_2$—CH(OH)—CH$_2$— and R" highly preferably denotes a hydrolysate obtained from cortex and/or cuticle of keratinic fibers. The product having the INCI name Laurdimonium Hydroxypropyl Hydrolyzed Keratin is most preferred.

The cationic keratin hydrolysates according to the present invention are contained in the compositions according to the present invention in a quantity from 0.01 to 10.0 wt %, preferably from 0.01 to 7.5 wt %, particularly preferably from 0.1 to 5.0 wt %, with reference to the total composition.

It is preferred according to the present invention if the compositions according to the present invention furthermore contain at least one quaternary compound. The effectiveness of the agent according to the present invention is thereby further enhanced, and the stability of the composition considerably promoted.

Quaternary ammonium compounds are, in principle, monomeric cationic or amphoteric ammonium compounds, monomeric amines, aminoamides, polymeric cationic ammonium compounds, and polymeric amphoteric ammonium compounds. From this plurality of possible quaternary ammonium compounds, the following groups have proven particularly suitable and are used, considered individually in each case, in a quantity from 0.1 to 10.0 wt %. This quantity does not exceed or fall below these values even when a mixture of different compounds of the quaternary ammonium compounds is used.

Esterquats in accordance with formula (Tkat1-2) constitute the first group:

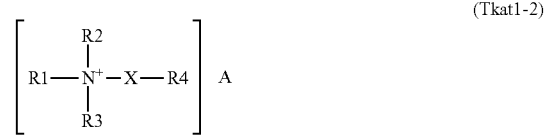

Residues R1, R2, and R3 therein are each mutually independent and can be identical or different. Residues R1, R2, and R3 signify:

a branched or unbranched alkyl residue having 1 to 4 carbon atoms, which can contain at least one hydroxyl group, or a saturated or unsaturated, branched or unbranched, or cyclic saturated or unsaturated alkyl residue having 6 to 30 carbon atoms, which can contain at least one hydroxyl group, or an aryl or alkaryl residue, for example phenyl or benzyl, the residue (—X—R4), provided that at most two of the residues R1, R2, or R3 can denote this residue.

The residue —(X—R4) is contained at least 1 to 3 times. In this, X denotes:

1) —(CH$_2$)$_n$—, where n=1 to 20, by preference n=1 to 10, and particularly preferably n=1 to 5, or 2) —(CH$_2$—CHR5-O)$_n$—, where n=1 to 200, by preference 1 to 100, particularly preferably 1 to 50, and particularly preferably 1 to 20, where R5 has the meaning of hydrogen, methyl, or ethyl, 3) a hydroxyalkyl group having one to four carbon atoms, which can be branched or unbranched and which contains at least one and at most 3 hydroxy groups. Examples of —X are: CHOH, —CHCH$_2$OH, —CH$_2$CHOH, —COHCHOH, —CHOHCOH, —CHCHOHCH$_3$, —CH$_2$COHCH$_3$, —CH$_2$CHOHCH$_2$, —C(CH$_2$OH)$_2$, —CH$_2$CHOHCH$_2$OH, —CH$_2$CH$_2$CHOH, —CH$_2$COHCH$_3$, and hydroxybutyl residues, where the bond from —X to R4 proceeds from the free valence of the relevant carbon atom, and R4 denotes:

1) R6-O—CO—, in which R6 is a saturated or unsaturated, branched or unbranched, or a cyclic saturated or unsaturated alkyl residue having 6 to 30 carbon atoms, which can contain at least one hydroxy group, and which optionally can be further oxyethylated with 1 to 100 ethylene oxide units and/or 1 to 100 propylene oxide units, or 2) R7-CO—, in which R7 is a saturated or unsaturated, branched or unbranched, or a cyclic saturated or unsaturated alkyl residue having 6 to 30 carbon atoms, which can contain at least one hydroxy group, and which optionally can be further oxyethylated with 1 to 100 ethylene oxide units and/or 1 to 100 propylene oxide units, and A denotes a physiologically acceptable organic or inorganic anion and is defined at this juncture representatively for all structures including those described hereinafter. The anion of all cationic compounds described is selected from the halide ions, fluoride, chloride, bromide, iodide, sulfates of the general formula $RSO_3^-$, in which R has the meaning of a saturated or unsaturated alkyl residue having 1 to 4 carbon atoms, or anionic residues of organic acids such as maleate, fumarate, oxalate, tartrate, citrate, lactate, or acetate.

Such products are marketed, for example, under the trademarks Rewoquat®, Stepantex®, Dehyquart®, Armocare®, and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90, and Akypoquat® 131 are examples of these esterquats.

Further compounds of formula (Tkat1-2) that are particularly preferred according to the present invention conform to formula (Tkat1-2.1), the cationic betaine esters

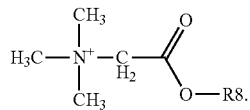

(Tkat1-2.1)

The meaning of R8 corresponds to that of R7.

The esterquats having the commercial names Armocare® VGH-70 as well as Dehyquart® F-75, Dehyquart® L80, Stepantex® VS 90, and Akypoquat® 131 are particularly preferred.

Quaternary imidazoline compounds are a further group. Formula (Tkat2) depicted below shows the structure of these compounds:

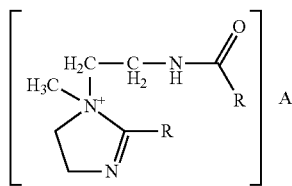

(Tkat2)

Residues R denote, mutually independently in each case, a saturated or unsaturated, linear or branched hydrocarbon residue having a chain length from 8 to 30 carbon atoms. The preferred compounds of formula (Tkat2) each contain the same hydrocarbon residue for R. The chain length of residues R is preferably 12 to 21 carbon atoms. "A" denotes an anion as described above. Examples that are particularly in accordance with the present invention are obtainable, for example, under the INCI names Quaternium-27, Quaternium-72, Quaternium-83, and Quatemium-91. Quaternium-91 is highly preferred according to the present invention.

In a particularly preferred embodiment of the invention the agents according to the present invention furthermore contain at least one amine and/or cationized amine, in particular an amidoamine and/or a cationized amidoamine, having the following structural formulas:

$$R1-NH-(CH_2)_n-N^+R^2R^3R^4 A$$  (Tkat3), in which R1 signifies an acyl or alkyl residue having 6 to 30 carbon atoms which can be branched or unbranched, saturated or unsaturated, and such that the acyl residue and/or the alkyl residue can contain at least one OH group, and R2, R3, and R4, mutually independently in each case, signify 1) hydrogen, or 2) an alkyl residue having 1 to 4 carbon atoms, which can be identical or different, saturated or unsaturated, and 3) a branched or unbranched hydroxyalkyl group having one to 4 carbon atoms, having at least one and at most three hydroxy groups, for example —$CH_2OH$, —$CH_2CH_2OH$, —$CHOHCHOH$, —$CH_2CHOHCH_3$, —$CH(CH_2OH)_2$, —$COH(CH_2OH)_2$, —$CH_2CHOHCH_2OH$, —$CH_2CH_2CH_2OH$, and hydroxybutyl residues, and A signifies an anion as described above, and n signifies an integer between 1 and 10.

A composition in which the amine and/or the quaternized amine according to the general formulas (Tkat3) is an amidoamine and/or a quaternized amidoamine, in which R1 signifies a branched or unbranched, saturated or unsaturated acyl residue having 6 to 30 carbon atoms, which can contain at least one OH group, is preferred. A fatty acid residue made of oils and waxes, in particular natural oils and waxes, is preferred here. Suitable examples thereof are lanolin, beeswax, or candelilla wax.

Also preferred are those amidoamines and/or quaternized amidoamines in which R2, R3, and/or R4 in formula (Tkat3) signify a residue according to the general formula $CH_2CH_2OR5$, in which R5 can have the meaning of alkyl residues having 1 to 4 carbon atoms, hydroxyethyl, or hydrogen. The preferred value of n in the general formula (Tkat8) is an integer between 2 and 5.

The alkylamidoamines both can be present as such, and can be converted by protonation in a correspondingly acid solution into a quaternary compound in the composition. The cationic alkylamidoamines are preferred according to the present invention.

Examples of commercial products of this kind according to the present invention are Witcamine® 100, Incromine® BB, Mackine® 401 and other Mackine® grades, Adogen® S18V and, as permanently cationic aminoamines: Rewoquat® RTM 50, Empigen® CSC, Swanol® Lanoquat DES-50, Rewoquat® UTM 50, Schercoquat® BAS, Lexquat® AMG-BEO, or Incroquat® Behenyl HE.

The cationic surfactants recited above can be used individually or in any desired combinations with one another, quantities between 0.01 and 10 wt %, preferably quantities from 0.01 to 7.5 wt %, and very particularly preferably quantities from 0.1 to 5.0 wt % being contained. The best results of all are obtained with quantities from 0.1 to 3.0 wt %, based in each case on the total composition of the respective agent.

Cationic and amphoteric polymers are further quaternary ammonium compounds.

The cationic and/or amphoteric polymers can be homo- or copolymers or polymers based on natural polymers, the quaternary nitrogen groups being contained either in the polymer chain or, by preference, as a substituent on one or more of the monomers. The ammonium-group-containing monomers can be copolymerized with non-cationic monomers. Suitable cationic monomers are unsaturated, radically polymerizable compounds that carry at least one cationic group, in particular ammonium-substituted vinyl monomers such as, for example, trialkylmethacryloxyalkylammonium, trialkylacryloxyalkylammonium, dialkyldiallylammonium, and quaternary vinylammonium monomers having cyclic groups containing cationic nitrogens, such as pyridinium, imidazolium, or quaternary pyrrolidones, e.g. alkylvinylimidazolium, alkylvinylpyridinium, or alkyvinylpyrrolidone salts. The alkyl groups of these monomers are by preference lower alkyl groups such as, for example, C1 to C7 alkyl groups, particularly preferably C1 to C3 alkyl groups.

The ammonium-group-containing monomers can be copolymerized with non-cationic monomers. Suitable comonomers are, for example, acrylamide, methacrylamide; alkyl and dialkyl acrylamide, alkyl and dialkyl methacrylamide, alkyl acrylate, alkyl methacrylate, vinylcaprolactone, vinylcaprolactam, vinylpyrrolidone, vinyl esters, e.g. vinyl acetate, vinyl alcohol, propylene glycol, or ethylene glycol, the alkyl groups of these monomers being by preference C1 to C7 alkyl groups, particularly preferably C1 to C3 alkyl groups.

From the plurality of these polymers, the following have proven to be particularly effective constituents of the active substance complex according to the present invention: homopolymers of the general formula —{$CH_2$—[$CR^1COO$—$(CH_2)_m N^+ R^2 R^3 R^4$]}$_n X^-$, in which $R^1$=—H or is —$CH_3$, $R^2$, $R^3$, and $R^4$ are selected mutually independently from C1 to 4 alkyl, alkenyl, or hydroxyalkyl groups, m=1, 2, 3, or 4, n is a natural number, and $X^-$ is a physiologically acceptable organic or inorganic anion. In the context of these polymers, the ones preferred according to the present invention are those for which at least one of the following conditions is valid: $R^1$ denotes a methyl group, $R^2$, $R^3$, and $R^4$ denote methyl groups, m has the value of 2.

Halide ions, sulfate ions, phosphate ions, methosulfate ions, as well as organic ions such as lactate, citrate, tartrate, and acetate ions are appropriate, for example, as physiologically acceptable counter ions $X^-$. Methosulfate and halide ions, in particular chloride, are preferred.

An amphoteric polymer highly preferred according to the present invention is a copolymer that has the following composition: 0.1 to 50%, by preference 10 to 50% (based on the total number of monomers in the copolymer) monomers of formula (Ia)

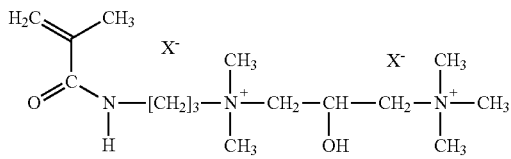

(Ia)

in which X denotes chloride, sulfate, methosulfate, and
monomers A2) from the group of acrylic acid, methacrylic acid, as well as the alkali metal and ammonium salts of said acids,
where monomers A2) account for 50 to 99.9%, by preference 50 to 90% of the copolymer (based on the total number of monomers in the copolymer).

A highly preferred polymer that is constructed as depicted above is obtainable commercially under the name Polyquaternium-74.

A particularly suitable homopolymer is the poly(methacryloyloxyethyltrimethylammonium) chloride (crosslinked, if desired) having the INCI name Polyquaternium-37. Such products are available commercially, for example, under the designations Rheocare® CTH (Cosmetic Rheologies) and Synthalen® CR (3V Sigma).

The homopolymer is used preferably in the form of a nonaqueous polymer dispersion. Polymer dispersions of this kind are obtainable commercially under the names Salcare® SC 95 and Salcare® SC 96.

Suitable cationic polymers that are derived from natural polymers are cationic derivatives of polysaccharides, for example cationic derivatives of cellulose, starch, or guar. Chitosan and chitosan derivatives are also suitable. Cationic polysaccharides have the general formula G-O—B—N+ $R_a R_b R_c A^-$ G is an anhydroglucose residue, for example starch anhydroglucose or cellulose anhydroglucose;
B is a divalent connecting group, for example alkylene, oxyalkylene, polyoxyalkylene, or hydroxyalkylene;
$R_a$, $R_b$ and $R_e$ mutually independently are alkyl, aryl, alkylaryl, arylalkyl, alkoxyalkyl, or alkoxyaryl each having up to 18 carbon atoms, the total number of carbon atoms in $R_a$, $R_b$, and $R_e$ by preference being a maximum of 20,
$A^-$ is a usual counter anion and is by preference chloride.

Cationic (i.e. quaternized) celluloses are obtainable on the market with different degrees of substitution, cationic charge density, nitrogen contents, and molecular weights. For example, Polyquaternium-67 is offered commercially under the names Polymer® SL or Polymer® SK (Amerchol). A further highly preferred cellulose is offered by the Croda company under the commercial name Mirustyle® CP. This is a Trimonium and Cocodimonium Hydroxyethylcellulose, constituting a derivatized cellulose, having the INCI-name Polyquaternium-72. Polyquaternium-72 can be used both in solid form and already predisssolved in aqueous solution.

Further cationic celluloses are available under the names Polymer JR® 400 (Amerchol, INCI name Polyquaternium-10) and Polymer Quatrisoft® LM-200 (Amerchol, INCI name Polyquaternium-24). Further commercial products are the compounds Celquat® H 100 and Celquat® L 200. Lastly, a further derivatized cellulose having the INCI name Polyquatemium-72 exists under the commercial name Mirustyle® CP of the Croda company, containing Trimonium and Cocodimonium Hydroxyethylcellulose. Polyquaternium-72 can be used both in solid form and already predisssolved in aqueous solution. Particularly preferred cationic celluloses are Polyquatemium-10, Polyquaternium-24, Polyquaternium-67, and Polyquaternium-72.

Suitable cationic guar derivatives are marketed under the commercial designation Jaguar® and have the INCI name Guar Hydroxypropyltrimonium Chloride. Particularly suitable cationic guar derivatives are additionally available commercially from the Hercules company under the designation N-Hance®. Further cationic guar derivatives are marketed by the Cognis company under the designation Cosmedia®. A preferred cationic guar derivative is the commercial product AquaCat® of the Hercules company. This raw material is a cationic guar derivative that is already predissolved. The cationic guar derivatives are preferred according to the present invention.

A suitable chitosan is marketed, for example, by the Kyowa Oil & Fat company, Japan, under the trade name Flonac®. A preferred chitosan salt is chitosonium pyrrolidonecarboxylate, which is marketed e.g. under the designation Kytamer® PC by the Amerchol company, USA. Further chitosan derivatives are readily available commercially under the commercial designations Hydagen® CMF, Hydagen® HCMF, and Chitolam® NB/101.

Further preferred cationic polymers are, for example:
cationic alkylpolyglycosides,
cationized honey, for example the commercial product Honeyquat® 50,
polymeric dimethyldiallylammonium salts and copolymers thereof with esters and amides of acrylic acid and methacrylic acid. The products obtainable commercially under the designations Merquat® 100 (poly(dimethyldiallylammonium chloride)) and Merquat® 550 (dimethyldiallylammonium chloride/acrylamide copolymer) are examples of such cationic polymers, having the INCI name Polyquaternium-7,
vinylpyrrolidone/vinylimidazolium methochloride copolymers, such as those offered under the designations Luviquat® FC 370, FC 550, and the INCI name Polyquaternium-16, as well as FC 905 and HM 552,
quaternized vinylpyrrolidone/dimethylaminoethyl methacrylate, for example vinylpyrrolidone/dimethylaminoethyl methacrylate methosulfate copolymer that is marketed under the commercial names Gafquat® 755 N and Gafquat® 734 by the GAF company, USA, and the INCI name Polyquaternium-11,
quaternized poly(vinylalcohol),
and the polymers known under the names Polyquaternium-2, Polyquaternium-17, Polyquaternium-18, and Polyquaternium-27, having quaternary nitrogen atoms in the main polymer chain,
vinylpyrrolidone/vinylcaprolactam/acrylate terpolymers such as those having acrylic acid esters and acrylic acid amides as a third monomer module, and offered commercially e.g. under the designation Aquaflex® SF 40.

Amphoteric polymers according to the present invention are those polymerizates in which a cationic group derives from at least one of the following monomers:
(i) monomers having quaternary ammonium groups of the general formula (Mono1)

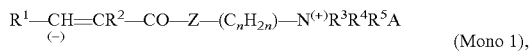

$$R^1\text{—}CH\text{=}CR^2\text{—}CO\text{—}Z\text{—}(C_nH_{2n})\text{—}N^{(+)}R^3R^4R^5 A^{(-)} \quad \text{(Mono 1)},$$

in which R1 and R2 mutually independently denote hydrogen or a methyl group and R3, R4, and R5 mutually independently denote alkyl groups having 1 to 4 carbon atoms, Z denotes an NH group or an oxygen atom, n is an integer from 2 to 5, and $A^{(-)}$ is the anion of an organic or inorganic acid,
(ii) monomers having quaternary ammonium groups of the general formula (Mono2)

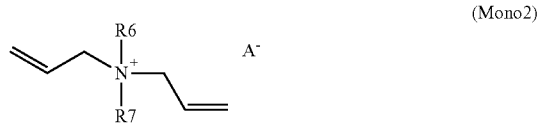

(Mono2)

in which $R^6$ and $R^7$ mutually independently denote a ($C_1$ to $C_4$) alkyl group, in particular a methyl group, and $A^-$ is the anion of an organic or inorganic acid,
(iii) monomeric carboxylic acids of the general formula (Mono3):

$$R^8\text{—}CH\text{=}CR^9\text{—}COOH \quad \text{(Mono3)}$$

in which $R^8$ and $R^9$ mutually independently are hydrogen or methyl groups.

Those polymerizates in which the monomers used are of type (i) in which $R^3$, $R^4$, and $R^5$ are methyl groups, Z is an NH group, and $A^{(-)}$ is a halide, methoxysulfate, or ethoxysulfate ion, are particularly preferred; acrylamidopropyltrimethylammonium chloride is a particularly preferred monomer (i). Acrylic acid is preferably utilized as monomer (ii) for the aforesaid polymerizates.

Particularly preferred amphoteric polymers are copolymers of at least one monomer (Mono1) and/or (Mono2) with the monomer (Mono3), in particular copolymers of monomers (Mono2) and (Mono3). Amphoteric polymers used very particularly preferably according to the present invention are copolymerizates of diallyldimethylammonium chloride and acrylic acid. These copolymerizates are marketed under the INCI name Polyquaternium-22, inter alia with the commercial name Merquat® 280 (Nalco).

Furthermore, the amphoteric polymers according to the present invention can additionally contain, alongside a monomer (Mono1) or (Mono2) and a monomer (Mono3), a monomer (Mono4)
(iv) monomeric carboxylic acid amides of the general formula (Mono4),

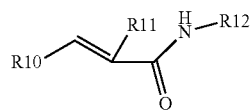

in which $R^{10}$ and $R^{11}$ mutually independently are hydrogen or methyl groups, and $R^{12}$ denotes a hydrogen atom or a ($C_1$ to $C_8$) alkyl group.

Amphoteric polymers based on a comonomer (Mono4) that are used very particularly preferably according to the present invention are terpolymers of diallyldimethylammonium chloride, acrylamide, and acrylic acid. These copolymerizates are marketed under the INCI name Polyquaternium-39, inter alia with the commercial name Merquat® Plus 3330 (Nalco), Amphoteric polymers can in general be used according to the present invention both directly and in a salt form that is obtained by neutralizing the polymerizates, for example using an alkali hydroxide.

The cationic polymers recited above can be used individually or in any combinations with one another, quantities between 0.01 and 10 wt %, preferably quantities from 0.01 to 7.5 wt %, and very particularly quantities from 0.1 to 5.0 wt % being contained. The best results of all are obtained with quantities from 0.1 to 3.0 wt %, based in each case on the total composition of the respective agent.

It is furthermore highly preferred according to the present invention if at least one amphoteric and/or zwitterionic surfactant is contained in the compositions according to the present invention. These compounds possibly contribute substantially to the stability of the cosmetic compositions.

Particularly suitable zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytic surfactants" (Tampho) are understood as those surface-active compounds that are capable of forming internal salts. Examples of suitable ampholytic surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, having in each case approximately 8 to 24 carbon atoms in the alkyl group. Typical examples of amphoteric or zwitterionic surfactants are alkyl betaines, alkylamidobetaines, aminopropionates, aminoglycinates, imidazolinium betaines, and sulfobetaines.

Particularly preferred ampholytic surfactants are N-cocalkylaminopropionate, cocacylaminoethylaminopropionate, and $C_{12}$ to $C_{18}$ acyl sarcosine. Coco Betaine is a particularly preferred compound.

These ingredients are used in quantities from 0.01 to 8.0 wt % in terms of the total composition of the agent. Quantities from 0.05 to 7.0 wt % are preferred. Quantities from 0.1 to 6.0 wt % are particularly preferred, and from 0.3 to 3.0 wt % are highly preferred.

All ingredients usual in cosmetic compositions can furthermore be added to this highly preferred basic framework of ingredients.

In addition to the obligatory silicones described above, the compositions according to the present invention can contain further silicones. These optional silicones are preferably at least one silicone polymer selected from the group of dimethiconols and/or the group of aminofunctional silicones and/or the group of dimethicones and/or the group of cyclomethicones.

The dimethicones according to the present invention can be both linear and branched, and also cyclic or cyclic and branched. Linear dimethicones can be represented by the following structural formula (Si1):

Branched dimethicones can be represented by the structural formula (Si1.1):

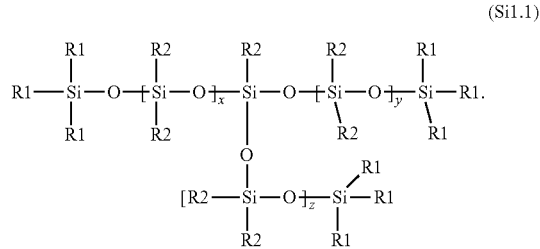

Residues $R^1$ and $R^2$ denote, mutually independently in each case, hydrogen, a methyl residue, a C2 to C30 linear, saturated or unsaturated hydrocarbon residue, a phenyl residue, and/or an aryl residue. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 and 3,000,000 cPs. The most preferred range is between 50,000 and 2,000,000 cPs. Viscosities around the range of approximately 60,000 cPs are highly preferred. Reference may be made here, for example to the product "Dow Corning 200, 60,000 cSt."

Particularly preferred cosmetic or dermatological preparations according to the present invention are characterized in that they contain at least one silicone of formula (Si1.2)

$$(CH_3)_3Si-[O-Si(CH_3)_2]_x-O-Si(CH_3)_3 \qquad (Si1.2),$$

in which x denotes a number from 0 to 100, by preference from 0 to 50, more preferably from 0 to 20, and in particular 0 to 10.

Dimethicones (Si1) are contained in the compositions according to the present invention in quantities from 0.01 to 10 wt %, by preference 0.01 to 8 wt %, particularly preferably 0.1 to 7.5 wt %, and in particular 0.1 to 5 wt %, based on the total composition.

Lastly, dimethiconols (Si8) are understood as silicone compounds. Dimethiconols according to the present invention can be both linear and branched, and also cyclic or cyclic and branched. Linear dimethiconols can be represented by the following structural formula (Si8-I):

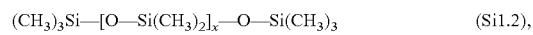

Branched dimethiconols can be represented by the structural formula (Si8-II):

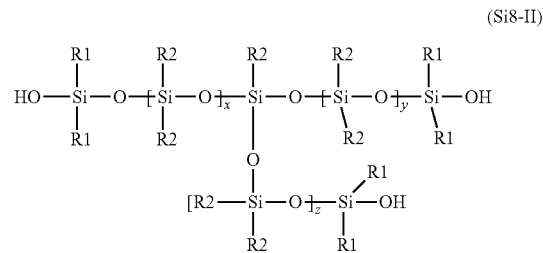

Residues $R^1$ and $R^2$ denote, mutually independently in each case, hydrogen, a methyl residue, a C2 to C30 linear, saturated or unsaturated hydrocarbon residue, a phenyl residue, and/or an aryl residue. The numbers x, y, and z are integers and range, mutually independently in each case, from 0 to 50,000. The molecular weights of the dimethicones are between 1000 D and 10,000,000 D. The viscosities are between 100 and 10,000,000 cPs, measured at 25° C. using a glass capillary viscosimeter in accordance with Dow Corning Corporate Test Method CTM 0004 of Jul. 20, 1970. Preferred viscosities are between 1000 and 5,000,000 cPs; very particularly preferred viscosities are between 10,000 and 3,000,000 cPs. The most preferred range is between 50,000 and 2,000,000 cPs.

The following commercial products are recited as examples of such products: Dow Corning 1-1254 Fluid, Dow Corning 2-9023 Fluid, Dow Corning 2-9026 Fluid, Abil OSW 5 (Degussa Care Specialties), Dow Corning 1401 Fluid, Dow Corning 1403 Fluid, Dow Corning 1501 Fluid, Dow Corning 1784 HVF Emulsion, Dow Corning 9546 Silicone Elastomer Blend, SM555, SM2725, SM2765, SM2785 (all four aforesaid GE Silicones), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforesaid Wacker-Chemie GmbH).

Dimethiconols (Si8) are in the compositions according to the present invention in quantities from 0.01 to 10 wt %, by preference 0.1 to 8 wt %, particularly preferably 0.1 to 7.5 wt %, and in particular 0.1 to 5 wt % dimethiconol, based on the composition.

Particularly preferred agents according to the present invention contain one or more aminofunctional silicones. Such silicones can be described, for example, by formula (Si-2)

$$M(R_a Q_b SiO_{(4-a-b)/2})_x (R_c SiO_{(4-c)/2})_y M \quad (Si\text{-}2);$$

in the above formula,

R is a hydrocarbon or a hydrocarbon residue having 1 to approximately 6 carbon atoms, Q is a polar residue of the general formula —$R^1HZ$, in which
  $R^1$ is a divalent connecting group that is bound to hydrogen and to the Z residue, assembled from carbon and hydrogen atoms, carbon, hydrogen, and oxygen atoms, or carbon, hydrogen, and nitrogen atoms, and
  Z is an organic aminofunctional residue that contains at least one aminofunctional group;

a assumes values in the range from approximately 0 to approximately 2, b assumes values in the range from approximately 1 to approximately 3, a+b is less than or equal to 3, and c is a number in the range from approximately 1 to approximately 3, and x is a number in the range from 1 to approximately 2,000, by preference from approximately 3 to approximately 50, and most preferably from approximately 3 to approximately 25, and y is a number in the range from approximately 20 to approximately 10,000, by preference from approximately 125 to approximately 10,000, and most preferably from approximately 150 to approximately 1,000, and M is a suitable silicone terminal group as known in the existing art, by preference trimethylsiloxy.

Z according to formula (Si-2) is an organic aminofunctional residue containing at least one functional amino group. One possible formula for the aforesaid Z is $NH(CH_2)_z NH_2$, in which z is an integer greater than or equal to 1. Another possible formula for the aforesaid Z is —$NH(CH_2)_z(CH_2)_{zz} NH$, in which both z and zz mutually independently are an integer greater than or equal to 1, said structure encompassing diamino ring structures such as piperazinyl. The aforesaid Z is most preferably an —$NHCH_2CH_2NH_2$ residue. Another possible formula for the aforesaid Z is —$N(CH_2)_z(CH_2)_{zz}NX_2$ or —$NX_2$, in which each X is selected independently of $X_2$ from the group consisting of hydrogen and alkyl groups having 1 to 12 carbon atoms, and zz is 0.

Q according to formula (Si-2) is most preferably a polar aminofunctional residue of the formula —$CH_2CH_2CH_2NHCH_2CH_2NH_2$.

In formula (Si-2), a assumes values in the range from 0 to 2, b assumes values in the range from 2 to 3, a+b is less than or equal to 3, and c is a number in the range from 1 to 3.

Cationic silicone oils such as, for example, the commercially obtainable products Dow Corning (DC) 929 Emulsion, DC2-2078, DC5-7113, SM-2059 (General Electric), and SLM-55067 (Wacker) are suitable according to the present invention.

Particularly preferred agents according to the present invention are characterized in that they contain at least one aminofunctional silicone of formula (Si3-a)

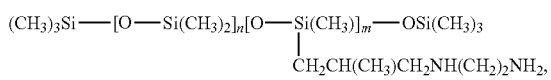
(Si-3a)

in which m and n are numbers whose sum (m+n) is between 1 and 2000, by preference between 50 and 150, where n assumes values by preference from 0 to 1999 and in particular from 49 to 149, and m by preference assumes values from 1 to 2000, in particular from 1 to 10.

These silicones are referred to according to the INCI declaration as Trimethylsilylamodimethicones and are obtainable, for example, under the designation Q2-7224 (manufacturer: Dow Corning; a stabilized trimethylsilylamodimethicone).

Also particularly preferred are agents according to the present invention that contain at least one aminofunctional silicone of formula (Si-3b)

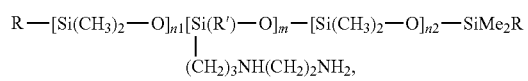
(Si-3b)

in which

R at least one R denotes —OH, a ($C_1$ to $C_{20}$) alkyl group, an ethoxylated and/or propoxylated ($C_1$ to $C_{20}$) alkoxy group, a methoxy group, an ethoxy group, or a —$CH_3$ group, R' denotes —OH, a ($C_1$ to $C_{20}$) alkoxy group, or a —$CH_3$ group, and m, n1, and n2 are numbers whose sum (m+n1+n2) is between 1 and 2000, by preference between 50 and 150, where the sum (n1+n2) assumes values by preference from 0 to 1999 and in particular from 49 to 149, and m by preference assumes values from 1 to 2000, in particular from 1 to 10.

These silicones are referred to according to the INCI declaration as Amodimethicones or as functionalized Amodimethicones, for example Bis(C13-15 Alkoxy) PG Amodimethicone (obtainable e.g. as a commercial product: DC 8500 of the Dow Corning company), Trideceth-9 PG-Amodimethicone (obtainable e.g. as a commercial product: Silcare® Silicone SEA of the Clariant company). Further commercial products are, for example, Wacker Belsil® ADM 652, Wacker Belsil® ADM 653, or Wacker Belsil® ADM 8020.

The cationic aminofunctional silicone polymers are contained in the compositions according to the present invention in quantities from 0.01 to 5 wt %, preferably in quantities from 0.05 to 5 wt %, and very particularly preferably in quantities from 0.1 to 5 wt %. The best results of all are obtained with quantities from 0.1 to 2.5 wt %, based in each case on the total composition of the respective agent.

Polyammonium-polysiloxane compounds are a further silicone according to the present invention having amino functions. Polyammonium-polysiloxane compounds can be acquired, for example, from GE Bayer Silicones under the commercial name Baysilone®. The products having the designations Baysilone TP 3911, SME 253, and SFE 839 are preferred in this context. It is very particularly preferred to use Baysilone TP 3911 as an active component of the compositions according to the present invention. Polyammonium-polysiloxane compounds are used in the compositions according to the present invention in a quantity from 0.01 to 10 wt %, by preference 0.01 to 7.5, particularly preferably 0.01 to 5.0 wt %, very particularly preferably from 0.05 to 2.5 wt %, referring in each case to the total composition.

The cyclic dimethicones referred to according to INCI as Cyclomethicones are also usable with preference according to the present invention. Preferred here are cosmetic or dermatological preparations according to the present invention that contain at least one silicone of formula (Si-4)

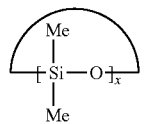
(Si-4)

in which x denotes a number from 3 to 200, by preference from 3 to 10, more preferably from 3 to 7, and in particular 3, 4, 5, or 6.

Agents likewise preferred according to the present invention are characterized in that they contain at least one silicone of formula (Si-5)

$R_3Si-[O-SiR_2]_x-(CH_2)_n-[O-SiR_2]_y-O-SiR_3$ (Si-5), in which R denotes identical or different residues from the group —H, phenyl, benzyl, —CH$_2$—CH(CH$_3$)Ph, C$_{1-20}$ alkyl residues, by preference —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and/or y denotes a number from 0 to 200, by preference from 0 to 10, more preferably from 0 to 7, and in particular 0, 1, 2, 3, 4, 5, or 6, and n denotes a number from 0 to 10, preferably from 1 to 8, and in particular 2, 3, 4, 5, 6.

Besides the dimethicones, dimethiconols, amodimethicones, and/or cyclomethicones according to the present invention, water-soluble silicones can be contained in the compositions according to the present invention as further silicones.

Corresponding hydrophilic silicones are selected, for example, from compounds of formulas (Si-6) and/or (Si-7). In particular, preferred silicone-based water-soluble surfactants are selected from the group of dimethicone copolyols, which are preferably alkoxylated, in particular polyethoxylated or polypropoxylated.

"Dimethicone copolyols" are understood according to the present invention preferably as polyoxyalkylene-modified dimethylpolysiloxanes of the general formulas (Si-6) or (Si-7):

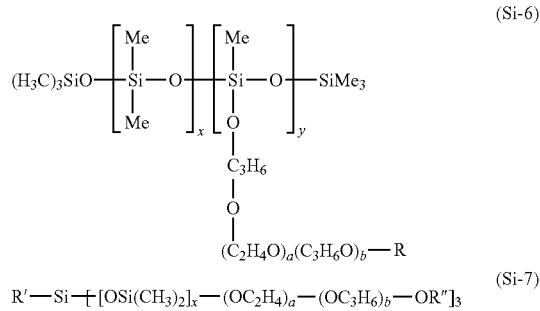
(Si-6)

$R'-Si+[OSi(CH_3)_2]_x-(OC_2H_4)_a-(OC_3H_6)_b-OR'']_3$ (Si-7)

in which residue R denotes a hydrogen atom, an alkyl group having 1 to 12 carbon atoms, an alkoxy group having 1 to 12 carbon atoms, or a hydroxyl group, residues R' and R" signify alkyl groups having 1 to 12 carbon atoms, x denotes an integer from 1 to 100, preferably from 20 to 30, y denotes an integer from 1 to 20, preferably from 2 to 10, and a and b denote integers from 0 to 50, preferably from 10 to 30.

Particularly preferred dimethicone copolyols for purposes of the invention are, for example, the products marketed commercially under the trade name SILWET (Union Carbide Corporation) and DOW CORNING. Dimethicone copolyols particularly preferred according to the present invention are Dow Corning 190 and Dow Corning 193.

Dimethicone copolyols are in the compositions according to the present invention in quantities from 0.01 to 10 wt %, by preference 0.01 to 8 wt %, particularly preferably 0.1 to 7.5 wt %, and in particular 0.1 to 5 wt % dimethicone copolyol based on the composition.

Ester oils can be contained with particular preference as oily substances in the active substance combination according to the present invention. Ester oils are defined as follows:

"Ester oils" are to be understood as esters of C$_6$ to C$_{30}$ fatty acids with C$_2$ to C$_{30}$ fatty alcohols. The monoesters of fatty acids with alcohols having 2 to 24 carbon atoms are preferred. Examples of fatty-acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. Examples of the fatty-alcohol components in the ester oils are isopropyl alcohol, capronyl alcohol, capryl alcohol, 2-ethylhexyl alcohol, caprinyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof. Isopropyl myristate (Rilanit® IPM), isononanoic acid C16-18 alkyl esters (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred according to the present invention.

The ester oils can of course also be alkoxylated with ethylene oxide, propylene oxide, or mixtures of ethylene oxide and propylene oxide. The alkoxylation can be located both on the fatty-alcohol part and on the fatty-acid part, and also on both parts, of the ester oils. It is preferred according to the present invention, however, if the fatty alcohol was first alkoxylated and then was esterified with fatty acid. Formula (D4-II) depicts these compounds in generalized fashion.

(D4-II)

R$^1$ here denotes a saturated or unsaturated, branched or unbranched, cyclic saturated or cyclic unsaturated acyl residue having 6 to 30 carbon atoms, AO denotes ethylene oxide, propylene oxide, or butylene oxide, X denotes a number between 1 and 200, by preference 1 and 100, particularly preferably between 1 and 50, very particularly preferably between 1 and 20, highly preferably between 1 and 10, and most preferably between 1 and 5, R2 denotes a saturated or unsaturated, branched or unbranched, cyclic saturated or cyclic unsaturated alkyl, alkenyl, alkinyl, phenyl, or benzyl residue having 6 to 30 carbon atoms. Examples of fatty-acid components used as residue R1 in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. Examples of the fatty-alcohol components as residue R2 in the ester oils are benzyl alcohol, isopropyl alcohol, capronyl alcohol, capryl alcohol, 2-ethylhexyl alcohol, caprinyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol, and brassidyl alcohol, as well as industrial mixtures thereof. An ester oil that is particularly preferred according to the present invention is obtainable, for example, under the INCI name PPG-3 Benzyl Ether Myristate.

Also to be understood as ester oils are:

dicarboxylic acid esters such as di-n-butyl adipate, di-(2-ethylhexyl) adipate, di-(2-ethylhexyl) succinate, and diisotridecyl acelaate, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate, as well as symmetrical, asymmetrical, or cyclic esters of carbonic acid with fatty alcohols, for example glycerol carbonate or dicaprylyl carbonate (Cetiol® CC), fatty acid triesters of saturated and/or unsaturated linear and/or branched fatty acids with glycerol, fatty acid partial glycerides, i.e. monoglycerides, diglycerides, and industrial mixtures thereof. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as industrial mixtures thereof. Oleic acid monoglycerides are preferably used.

Ester oils are used in the agents according to the present invention in a quantity from 0.01 to 20 wt %, preferably 0.01 to 10.0 wt %, particularly preferably 0.01 to 7.5 wt %, highly preferably from 0.1 to 5.0 wt %. It is of course also possible according to the present invention to use several ester oils simultaneously.

Further oily substances according to the present invention are:

Vegetable oils. Examples of such oils are sunflower oil, olive oil, soy oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as di-tert-butyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (Cetiol® S) and di-n-octyl ether (Cetiol® OE), available as commercial products, can be preferred.

Natural oils that can be used are, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, cocoa butter, linseed oil, *macadamia* nut oil, corn oil, almond oil, marula oil, evening primrose oil, olive oil, palm oil, rapeseed oil, rice oil, sea buckthorn pulp oil, sea buckthorn seed oil, sesame oil, shea butter, soy oil, sunflower oil, grapeseed oil, walnut oil, wheat germ oil, or wild rose oil.

The hair treatment agents according to the present invention of course also contain, besides the active substance combination according to the present invention, further constituents usual in cosmetic compositions. Selection of these constituents is generally based on the intended use of the hair treatment agents. In the case of a shampoo, for example, further surface-active substances will be contained. In the case of hair treatments, further cationic compounds and further care-providing substances will be optionally contained. In many cases the agents contain at least one surface-active substance, both anionic as well as zwitterionic, ampholytic, nonionic, and cationic surface-active substances being suitable in principle. Selection of the surface-active substances is based on the nature of the agent.

All anionic surface-active substances suitable for use on the human body are suitable as anionic surfactants (Tanion) in preparations according to the present invention. Typical examples of anionic surfactants are:

linear and branched fatty acids having 8 to 30 carbon atoms (soaps), ether carboxylic acids of the formula R—O—(CH$_2$—CH$_2$O)$_x$—CH$_2$—COOH, in which R is a linear alkyl group having 8 to 30 carbon atoms and x=0 or is 1 to 16, and salts thereof, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic acid mono- and dialkyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups, linear alkanesulfonates having 8 to 24 carbon atoms;

linear alpha-olefinsulfonates having 8 to 24 carbon atoms, alpha-sulfo fatty acid methyl esters of fatty acids having 8 to 30 carbon atoms, alkyl sulfates and alkyl polyglycol ether sulfates of the formula R—O(CH$_2$—CH$_2$—O)$_x$—OSO$_3$H, in which R is a preferably linear alkyl group having 8 to 30 carbon atoms and x=0 or is 1 to 12, hydroxysulfonates substantially corresponding to at least one of the two following formulas, or mixtures thereof, as well as salts thereof:

$CH_3$—$(CH_2)_y$—CHOH—$(CH_2)_p$—(CH—$SO_3$M)-$(CH_2)_z$—$CH_2$—O—$(C_nH_{2n}O)_x$—H, and/or $CH_3$—$(CH_2)_z$—(CH—$SO_3$M)-$(CH_2)_p$—CHOH—$(CH_2)_y$—$CH_2$—O—$(C_nH_{2n}O)_x$—H, where in both formulas y and z=0 or are integers from 1 to 18, p=0, 1, or 2, and the sum (y+z+p) is a number from 12 to 18, x=0 or is a number from 1 to 30, and n is an integer from 2 to 4, and M=hydrogen or alkali, in particular sodium, potassium, lithium, alkaline earth, in particular magnesium, calcium, zinc, and/or an ammonium ion, which optionally can be substituted, in particular mono-, di-, tri- or tetraammonium ions having C1 to C4 alkyl, alkenyl, or aryl residues, sulfated hydroxyalkylpolyethylene glycol ethers and/or hydroxyalkylenepropylene glycol ethers of the formula $R^1$—(CHO$SO_3$M)-CH$R^3$—(OCH$R^4$—$CH_2)_n$—$OR^2$, where $R^1$ denotes a linear alkyl residue having 1 to 24 carbon atoms, $R^2$ a linear or branched, saturated alkyl residue having 1 to 24 carbon atoms, $R^3$ denotes hydrogen or a linear alkyl residue having 1 to 24 carbon atoms, $R^4$ denotes hydrogen or a methyl residue, and M denotes hydrogen, ammonium, alkylammonium, alkanolammonium, in which the alkyl and alkanol residues each comprise 1 to 4 carbon atoms, or a metal atom selected from lithium, sodium, potassium, calcium, or magnesium, and n denotes a number in the range from 0 to 12, and furthermore the total number of carbon atoms contained in $R^1$ and $R^3$ is 2 to 44, sulfonates of unsaturated fatty acids having 8 to 24 carbon atoms and 1 to 6 double bonds, esters of tartaric acid and citric acid with alcohols that represent addition products of approximately 2 to 15 molecules of ethylene oxide and/or propylene oxide with fatty alcohols having 8 to 22 carbon atoms, alkyl and/or alkenyl ether phosphates of the formula

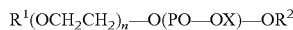

in which $R^1$ preferably denotes an aliphatic hydrocarbon residue having 8 to 30 carbon atoms, $R^2$ denotes hydrogen, a $(CH_2CH_2O)_1R^2$ residue, or X, n denotes numbers from 1 to 10, and X denotes hydrogen, an alkali or alkaline-earth metal, or $NR^3N^4N^5N^6$, where $R^3$ to $R^6$ mutually independently denote hydrogen or a $C_1$ to $C_4$ hydrocarbon residue, sulfated fatty acid alkylene glycol esters of the formula RCO(AlkO)$_n$$SO_3$M, in which RCO— denotes a linear or branched, aliphatic, saturated and/or unsaturated acyl residue having 6 to 22 carbon atoms, Alk denotes $CH_2CH_2$, CH$CH_3$$CH_2$, and/or $CH_2$CH$CH_3$, n denotes numbers from 0.5 to 5, and M denotes a metal, such as an alkali metal, in particular sodium, potassium, lithium, an alkaline-earth metal, in particular magnesium, calcium, zinc, or an ammonium ion such as $^+NR^3N^4N^5N^6$, where $R^3$ to $R^6$ mutually independently denote hydrogen or a $C_1$ to $C_4$ hydrocarbon residue, monoglyceride sulfates and monoglyceride ether sulfates of the formula $R^8$OC—(OCH$_2$CH$_2$)$_x$-OCH$_2$—[CHO(CH$_2$CH$_2$O)$_y$H]—CH$_2$O(CH$_2$CH$_2$O)$_z$—$SO_3$X, in which $R^8$CO denotes a linear or branched acyl residue having 6 to 22 carbon atoms, x, y, and z in total denote 0 or numbers from 1 to 30, preferably 2 to 10, and X denotes an alkali or alkaline-earth metal. Typical examples of monoglyceride (ether) sulfates suitable for purposes of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride, and their ethylene oxide adducts with sulfur trioxide or chlorosulfonic acid in the form of their sodium salts. It is preferable to use monoglyceride sulfates in which $R^8$CO denotes a linear acyl residue having 8 to 18 carbon atoms, amide ether carboxylic acids, $R^1$—CO—$NR^2$—$CH_2CH_2$—O—$(CH_2CH_2O)_n$$CH_2$COOM, where $R^1$ is a straight-chain or branched alkyl or alkenyl residue having a number of carbon atoms in the chain from 2 to 30, n denotes an integer from 1 to 20, and $R^2$ denotes hydrogen, a methyl, ethyl, propyl, isopropyl, n-butyl, tert-butyl, or isobutyl residue and M denotes hydrogen or a metal, such as an alkali metal, in particular sodium, potassium, lithium, an alkaline-earth metal, in particular magnesium, calcium, zinc, or an ammonium ion, such as $^+NR^3N^4N^5N^6$, where $R^3$ to $R^6$ mutually independently denote hydrogen or a $C_1$ to $C_4$ hydrocarbon residue. Products of this kind are obtainable, for example, from the Chem-Y company under the product designation Akypo®.

Acyl glutamates of the formula XOOC—$CH_2CH_2$CH(C(NH)OR)—COOX, in which RCO denotes a linear or branched acyl residue having 6 to 22 carbon atoms and 0 and/or 1, 2, or 3 double bonds, and X denotes hydrogen, an alkali and/or alkaline-earth metal, ammonium, alkylammonium, alkanolammonium, or glucammonium, condensation products of a water-soluble salt of a water-soluble protein hydrolysate with a C8 to C30 fatty acid. Such products have been commercially obtainable for some time under the trade names Lamepon, Maypon®, Gluadin®, Hostapon® KCG, or Amisoft®, alkyl- and/or alkenyloligoglycoside carboxylates, sulfates, phosphates, and/or isethionates, acyl lactylates, and hydroxy mixed ether sulfates.

If the mild anionic surfactants contain polyglycol ether chains, it is very particularly preferred that they exhibit a restricted homolog distribution. It is further preferred in the case of mild anionic surfactants having polyglycol ether units that the number of glycol ether groups be equal to 1 to 20, preferably 2 to 15, particularly preferably 2 to 12. Particularly mild anionic surfactants having polyglycol ether groups without a restricted homolog distribution can also be obtained, for example, if on the one hand the number of polyglycol ether groups is equal to 4 to 12, and Zn or Mg ions are selected as a counter ion. One example thereof is the commercial product Texapon® ASV.

Nonionic surfactants (Tnio) are, for example, addition products of 2 to 50 mol ethylene oxide and/or 0 to 5 mol propylene oxide with linear and branched fatty alcohols having 6 to 30 carbon atoms, fatty alcohol polyglycol ethers, fatty alcohol polypropylene glycol ethers, or mixed fatty alcohol polyethers, addition products of 2 to 50 mol ethylene oxide and/or 0 to 5 mol propylene oxide with linear and branched fatty acids having 6 to 30 carbon atoms, the fatty acid polyglycol ethers, fatty acid polypropylene glycol ethers, or mixed fatty acid polyethers, addition products of 2 to 50 mol ethylene oxide and/or 0 to 5 mol propylene oxide with linear and branched alkylphenols having 8 to 15 carbon atoms in the alkyl group, the alkylphenol polyglycol ethers, alkylphenol polypropylene glycol ethers, or mixed alkylphenol polyethers, addition products, end-capped with a methyl or $C_2$ to $C_6$ alkyl group, of 2 to 50 mol ethylene oxide and/or 0 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydrol® LS, Dehydrol® LT (Cognis), $C_{12}$ to $C_{30}$ fatty acid mono- and diesters of addition products of 1 to 30 mol ethylene oxide with glycerol, addition products of 5 to 60 mol ethylene oxide with castor oil and hardened castor oil, polyol fatty acid esters such as, for example, the commercial product Hydagen® HSP (Cognis), or Sovermol® grades (Cognis), alkoxylated triglycerides, alkoxylated fatty acid alkyl esters of formula (Tnio-I):

$$R^1CO-(OCH_2CHR^2)_w OR^3 \qquad \text{(Tnio-I),}$$

in which $R^1CO$ denotes a linear or branched, saturated and/or unsaturated acyl residue having 6 to 22 carbon atoms, $R^2$ denotes hydrogen or methyl, $R^3$ denotes linear or branched alkyl residues having 1 to 4 carbon atoms, and w denotes numbers from 1 to 20, amine oxides, hydroxy mixed ethers, $R^1O[CH_2CH(CH_3)O]_x(CH_2CHR^2O)_y[CH_2CH(OH)R^3]_z$ where $R^1$ denotes a linear or branched, saturated or unsaturated alkyl and/or alkenyl residue having 2 to 30 carbon atoms, $R^2$ denotes hydrogen, a methyl, ethyl, propyl, or isopropyl residue, $R^3$ denotes a linear or branched alkyl residue having 2 to 30 carbon atoms, x denotes 0 or a number from 1 to 20, Y denotes a number from 1 to 30, and z denotes the number 1, 2, 3, 4 or 5, sorbitan fatty acid esters and addition products of ethylene oxide with sorbitan fatty acid esters, for example polysorbates, sugar fatty acid esters and addition products of ethylene oxide with sugar fatty acid esters, addition products of ethylene oxide with fatty acid alkanolamides and fatty amines, sugar surfactants of the alkyl- and alkenyloligoglycoside types, sugar surfactants of the fatty acid N-alkylpolyhydroxyalkylamide types, fatty acid amide polyglycol ethers, fatty amine polygycol ethers, mixed ethers, mixed formals and polysorbates.

Cationic surfactants of formula (Tkat1-1) can additionally be used and are different from the ingredients described as obligatory cationic surfactants.

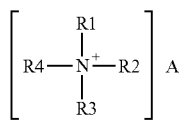
(Tkat1)

In formula (Tkat1), R1, R2, R3, and R4, mutually independently in each case, denote hydrogen, a methyl group, a phenyl group, a benzyl group, a saturated, branched or unbranched alkyl residue having a chain length from 8 to 30 carbon atoms, which optionally can be substituted with one or more hydroxy groups. "A" denotes a physiologically acceptable anion, for example halides such as chloride or bromide, as well as methosulfates.

Examples of compounds of formula (Tkat1) are lauryltrimethylammonium chloride, cetyltrimethylammonium chloride, cetyltrimethylammonium bromide, cetyltrimethylammonium metho sulfate, dicetyldimethylammonium chloride, tricetylmethylammonium chloride, stearyltrimethylammonium chloride, distearyldimethylammonium chloride, lauryldimethylbenzylammonium chloride, behenyltrimethylammonium chloride, behenyltrimethylammonium bromide, behenyltrimethylammonium methosulfate.

Surfactants (T) are used in quantities from 0.05 to 45 wt %, preferably 0.1 to 30 wt %, and very particularly preferably from 0.5 to 25 wt %, based on the total agent used according to the present invention.

Emulsifier agents usable according to the present invention are, for example:

addition products of 4 to 30 mol ethylene oxide and/or 0 to 5 mol propylene oxide with linear fatty alcohols having 8 to 22 carbon atoms, with fatty acids having 12 to 22 carbon atoms, and with alkylphenols having 8 to 15 carbon atoms in the alkyl group, $C_{12}$ to $C_{22}$ fatty acid mono- and diesters of addition products of 1 to 30 mol ethylene oxide with polyols having 3 to 6 carbon atoms, in particular with glycerol, addition products of ethylene oxide and polyglycerol with methylglucoside fatty acid esters, fatty acid alkanolamides, and fatty acid glucamides, $C_8$ to $C_{22}$ alkylmono- and oligoglycosides and ethoxylated analogs thereof, where degrees of oligomerization from 1.1 to 5, in particular 1.2 to 2.0, and glucose as a sugar component, are preferred, mixtures of alkyl(oligo)glucosides and fatty alcohols, for example the commercially obtainable product Montanov® 68, addition products of 5 to 60 mol ethylene oxide with castor oil and hardened castor oil, partial esters of polyols having 3 to 6 carbon atoms with saturated fatty acids having 8 to 22 carbon atoms, sterols, both from animal tissue (zoosterols, cholesterol, lanosterol) and from vegetable fats (phytosterols, ergosterol, stigmasterol, sitosterol), or from fungi and yeasts (mycosterols), phospholipids (lecithins, phosphatidylcholines), fatty acid esters of sugars and sugar alcohols, such as sorbitol, polyglycerols and polyglycerol derivatives such as e.g. polyglycerol-12-hydroxystearate (commercial product Dehymuls® PGPH).

The agents according to the present invention contain emulsifier agents preferably in quantities from 0.1 to 25 wt %, in particular 0.5 to 15 wt %, based on the total agent.

With particular preference, the compositions according to the present invention contain fatty substances (Fat) as a further active substance. "Fatty substances" (Fat) are to be understood as fatty acids, fatty alcohols, natural and synthetic waxes, which can be present both in solid form and in liquid form in aqueous dispersion, and natural and synthetic cosmetic oil components.

The fatty acids (Fatac) that can be used are linear and/or branched, saturated and/or unsaturated fatty acids having 6 to 30 carbon atoms. Fatty acids having 10 to 22 carbon atoms are preferred. Among those that might be recited are, for example, isostearic acids, such as the commercial products Emersol® 871 and Emersol® 875, and isopalmitic acids such as the commercial product Edenor® IP 95, as well as all other fatty acids marketed under the Edenor® commercial designations (Cognis). Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid, and erucic acid, as well as industrial mixtures thereof. The fatty acid cuts that are obtainable from coconut oil or palm oil are usually particularly preferred; the use of stearic acid is, as a rule, particularly preferred.

The quantity used is 0.1 to 15 wt % based on the total agent. The quantity is preferably 0.5 to 10 wt %, and quantities from 1 to 5 wt % can be very particularly advantageous.

Fatty alcohols (Fatal) that can be used are saturated, mono- or polyunsaturated, branched or unbranched fatty alcohols having $C_6$ to $C_{30}$, preferably $C_{10}$ to $C_{22}$, and very particularly preferably $C_{12}$ to $C_{22}$ carbon atoms. Usable in the context of the invention are, for example, decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, caprinyl alcohol, linoleyl alcohol, linolenyl alcohol, and behenyl alcohol, as well as Guerbet alcohols thereof, this listing being intended to be exemplary and not limiting in nature. Fatty alcohols derive, however, from preferably natural fatty acids; it is usually possible to proceed by recovery from esters of the fatty acids by reduction. Also usable according to the present invention are those fatty alcohol cuts that represent a mixture of different fatty alcohols. Such substances are, for example, available for purchase under the designations Stenol®, e.g. Stenol® 1618, or Lanette®, e.g. Lanette® O, or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16, or Isocarb® 24. It is of course also possible according to the present invention to use wool-wax alcohols such as those available for purchase under the designations Corona®, White Swan®, Coronet®, or Fluilan®. The fatty alcohols are used in quantities from 0.1 to 30 wt % based on the total preparation, preferably in quantities from 0.1 to 20 wt %.

Natural or synthetic waxes (Fatwax) that can be used according to the present invention are solid paraffins or isoparaffins, carnauba waxes, beeswaxes, candelilla waxes, ozocerites, ceresin, spermaceti, sunflower wax, fruit waxes such as, for example, apple wax or citrus wax, microcrystalline waxes made from PE or PP. Such waxes are obtainable, for example, via Kahl & Co., Trittau.

The quantity used is 0.1 to 50 wt % based on the total agent, preferably 0.1 to 20 wt %, and particularly preferably 0.1 to 15 wt % based on the total agent.

The total quantity of oil and fat components in the agents according to the present invention is usually 0.5 to 75 wt % based on the total agent. Quantities from 0.5 to 35 wt % are preferred according to the present invention.

Protein hydrolysates and/or derivatives thereof are a further synergistic active substance according to the present invention in the compositions according to the present invention having the active substance complex according to the present invention.

According to the present invention, protein hydrolysates of both vegetable and animal origin, or of marine or synthetic origin, can be used.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), and Kerasol® (Croda).

Also preferred according to the present invention are vegetable protein hydrolysates such as, for example, soy, almond, pea, moringa, potato, and wheat protein hydrolysates. Such products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), Crotein® (Croda), and Puricare® LS 9658 of the Laboratoires Sérobiologiques company.

Further protein hydrolysates preferred according to the present invention are of marine origin. These include, for example, collagen hydrolysates from fish or algae, as well as protein hydrolysates from mussels and/or pearl hydrolysates. Examples of pearl extracts according to the present invention are the commercial products Pearl Protein Extract BG® or Crodarom® Pearl.

Cationized protein hydrolysates are further to be included among the protein hydrolysates and derivatives thereof, in which context the underlying protein hydrolysate can derive from animals, for example from collagen, milk, or keratin, from plants, for example from wheat, corn, rice, potatoes, soy, or almonds, from marine life forms, for example from fish collagen or algae, or from biotechnologically obtained protein hydrolysates. Typical examples that may be recited of cationic protein hydrolysates and derivatives according to the present invention are the products listed under the INCI names in the "International Cosmetic Ingredient Dictionary and Handbook" (seventh edition 1997, The Cosmetic, Toiletry, and Fragrance Association, 1101 17th Street, N.W., Suite 300, Washington, D.C. 20036-4702) and available commercially.

Protein hydrolysates are contained in the compositions in concentrations from 0.001 wt % to 20 wt %, by preference from 0.05 wt % to 15 wt %, and very particularly preferably in quantities from 0.05 wt % to 5 wt %.

A further group of preferred ingredients, the amino acids and oligopeptides, is closely related to protein hydrolysates structurally and in terms of spectrum of action. In the present Application the term "amino acid" is also understood as a structure that contains only one permanent cationic group in the molecule, such as e.g. choline. Also understood under this term are substances such as carnitine or taurine, since they, like amino acids, occur naturally in biological systems and in many cases behave like amino acids.

Amino acids according to the present invention are selected from alanine, arginine, asparagine, aspartic acid, cysteine, cystine, citrulline, glutamic acid, glutamine, glycine, histidine, hydroxylysine, hydroxyproline, isoleucine, leucine, lysine, methionine, phenylalanine, proline, serine, threonine, thyroxine, tryptophan, tyrosine, acetyltyrosine, valine, betaine, ornithine, 1,1-dimethylproline, hercynine (Nα,Nα,Nα-trimethyl-L-histidinium betaine), ergothioneine (thioneine, 2-mercapto-Nα,Nα,Nα-trimethyl-L-histidinium betaine), carnitine, taurine, and choline, as well as mixtures thereof. All types of isomers can be used according to the present invention, for example diastereomers, enantiomers, cis-trans isomers, optical isomers, conformation isomers, and racemates.

Alanine, arginine, asparagine, citrulline, glutamic acid, glutamine, glycine, histidine, hydroxylysine, hydroxyproline, isoleucine, leucine, lysine, proline, serine, betaine, ornithine, acetyltyrosine, 1,1-dimethylproline, carnitine, taurine, choline, and mixtures thereof are used with particular preference.

Arginine, citrulline, glutamine, glycine, histidine, lysine, proline, serine, betaine, ornithine, carnitine, taurine, acetyltyrosine, and mixtures thereof are very particularly preferably used.

Highly preferably, arginine, citrulline, glutamine, histidine, lysine, acetyltyrosine, ornithine, carnitine, and taurine, and mixtures thereof, are used.

Mostly highly preferred are arginine, citrulline, glutamine, acetyltyrosine, ornithine, carnitine, and taurine, as well as mixtures of
arginine and taurine,
glutamine and taurine,
glutamine and carnitine,
arginine and glutamine,
carnitine and taurine, as well as mixtures of
arginine, carnitine, and taurine,
glutamine, carnitine, and taurine, and
arginine, acetyltyrosine, ornithine, and citrulline.

Oligopeptides for purposes of the present Application are condensation products of amino acids, linked by peptide bonds in the manner of an acid amide, encompassing at least 3 and at most 25 amino acids. In hair treatment agents preferred according to the present invention the oligopeptide encompasses 5 to 15 amino acids, by preference 6 to 13 amino acids, particularly preferably 7 to 12 amino acids, and in particular 8, 9, or 10 amino acids.

Oligopeptides particularly preferred according to the present invention comprise at least the Glu-Glu-Glu sequence. The molar mass of the oligopeptide contained in the agents according to the present invention can vary depending on whether further amino acids are bound to the Glu-Glu-Glu sequence, and depending on the nature of those amino acids. Hair treatment agents preferred according to the present invention are characterized in that the oligopeptide has a molar mass from 650 to 3000 Da, by preference from 750 to 2500 Da, particularly preferably from 850 to 2000 Da, and in particular from 1000 to 1600 Da, and comprises at least the preferred Glu-Glu-Glu sequence.

As is evident from the preferred number of amino acids in the oligopeptides and from the preferred molar mass range, it is preferred to use oligopeptides that are not made up only of the three glutamic acids but instead have further amino acids bound to that sequence. These further amino acids are selected by preference from specific amino acids, while specific other representatives are less preferred according to the present invention.

It is preferred, for example, if the oligopeptides used in the agents according to the present invention contain no methionine. It is further preferred if the oligopeptides used in the agents according to the present invention contain no cysteine and/or cystine. It is further preferred if the oligopeptides used in the agents according to the present invention contain no aspartic acid and/or asparagine. It is further preferred if the oligopeptides used in the agents according to the present invention contain no serine and/or threonine.

Conversely, it is preferred if the oligopeptides used in the agents according to the present invention contain tyrosine. It is further preferred if the oligopeptides used in the agents according to the present invention contain leucine. It is further preferred if the oligopeptides used in the agents according to the present invention contain isoleucine. It is further preferred if the oligopeptides used in the agents according to the present invention contain arginine. It is further preferred if the oligopeptides used in the agents according to the present invention contain valine.

Particularly preferred oligopeptides and amino acid sequences contained in the preferred oligopeptides are described below:

A particularly preferred oligopeptide additionally contains tyrosine, which is bound preferably via its acid function to the Glu-Glu-Glu sequence. Hair treatment agents preferred according to the present invention are therefore characterized in that the oligopeptide contained in them comprises at least one Tyr-Glu-Glu-Glu amino acid sequence, such that the amino group can be present in free or protonated form, and the carboxy groups can be present in free or deprotonated form.

A further particularly preferred oligopeptide additionally contains isoleucine, which is bound preferably via its amino function to the Glu-Glu-Glu sequence. Hair treatment agents preferred according to the present invention are therefore characterized in that the oligopeptide contained in them comprises at least one Glu-Glu-Glu-Ile amino acid sequence, such that the amino group can be present in free or protonated form, and the carboxy groups can be present in free or deprotonated form.

Oligopeptides that comprise the two aforesaid amino acids (tyrosine and isoleucine) are preferred according to the present invention. Particularly preferred in this context are hair treatment agents according to the present invention in which the oligopeptide contained in them comprises at least one Tyr-Glu-Glu-Glu-Ile amino acid sequence, such that the amino group can be present in free or protonated faun, and the carboxy groups can be present in free or deprotonated form.

Further preferred oligopeptides additionally contain arginine, which is preferably present bound to isoleucine. A highly preferred oligopeptide is obtainable commercially from the Croda company under the commercial name ProSina®.

The hair treatment agents according to the present invention contain the selected amino acids and/or the selected oligopeptides as described above in a total quantity, based on the total agent, from 0.0001 to 10.0 wt %, particularly preferably from 0.0001 to 7.0 wt %, very particularly preferably from 0.0001 to 5.0 wt %.

A further preferred group of ingredients of the compositions according to the present invention is vitamins, provitamins, or vitamin precursors. Vitamins, provitamins, and vitamin precursors that are allocated to groups A, B, C, E, F, and H are particularly preferred.

The group of substances referred to as "vitamin A" includes retinol (vitamin $A_1$) as well as 3,4-didehydroretinol (vitamin $A_2$). β-Carotene is the provitamin of retinol. Vitamin A components that are suitable according to the present invention are, for example, vitamin A acid and esters thereof, vitamin A aldehyde, and vitamin A alcohol, as well as esters thereof such as the palmitate and acetate. The agents according to the present invention contain the vitamin A component preferably in quantities from 0.05 to 1 wt %, based on the total preparation.

Members of the vitamin B group or vitamin B complex are, among others:

Vitamin $B_1$ (thiamine)
Vitamin $B_2$ (riboflavin)
Vitamin $B_3$. The compounds nicotinic acid and nicotinic acid amide (niacinamide) are often listed under this designation. Nicotinic acid amide is preferred according to the present invention; it is contained in the agents used according to the present invention preferably in quantities from 0.05 to 1 wt % based on the total agent.

Vitamin B$_5$ (pantothenic acid, panthenol, and pantolactone). In the context of this group, panthenol and/or pantolactone are preferably used. Derivatives of panthenol that are usable according to the present invention are, in particular, the esters and ethers of panthenol as well as cationically derivatized panthenols. Individual representatives are, for example, panthenol triacetate, panthenol monoethyl ether and the monoacetate thereof, as well as cationic panthenol derivatives.

Pantothenic acid is used in the present invention preferably as a derivative in the form of more-stable calcium salts and sodium salts (calcium pantothenate, sodium pantothenate).

Vitamin B$_6$ (pyridoxine as well as pyridoxamine and pyridoxal).

The aforesaid compounds of the vitamin B type, in particular vitamin B$_3$, B$_5$, and B$_6$, are contained in the agents according to the present invention preferably in quantities from 0.05 to 10 wt % based on the total agent. Quantities from 0.1 to 5 wt % are particularly preferred.

Vitamin C (ascorbic acid). Vitamin C is utilized in the agents according to the present invention preferably in quantities from 0.1 to 3 wt % based on the total agent. Utilization in the form of the palmitic acid ester, glucosides, or phosphates can be preferred. Utilization in combination with tocopherols can likewise be preferred.

Vitamin E (tocopherols, in particular α-tocopherol). Tocopherol and its derivatives, which include in particular esters such as the acetate, nicotinate, phosphate, and succinate, are contained in the agents according to the present invention preferably in quantities from 0.05 to 1 wt % based on the total agent.

Vitamin F. The term "vitamin F" is usually understood to mean essential fatty acids, in particular linoleic acid, linolenic acid, and arachidonic acid.

Vitamin H. "Vitamin H" refers to the compound (3aS,4S,6aR)-2-oxohexahydrothienol[3,4-d]-imidazole-4-valeric acid, for which the trivial name "biotin" has, however, now become established. Biotin is contained in the agents according to the present invention preferably in quantities from 0.0001 to 1.0 wt %, in particular in quantities from 0.001 to 0.01 wt %.

The compositions according to the present invention preferably contain vitamins, provitamins, and vitamin precursors from groups A, B, E, and H. Panthenol, pantolactone, pyridoxine and its derivatives, as well as nicotinic acid amide and biotin, are particularly preferred.

In a further embodiment preferred according to the present invention, the compositions according to the present invention contain bioquinones. In agents according to the present invention, "suitable bioquinones" are to be understood as one or more ubiquinone(s) and/or plastoquinone(s). The ubiquinones preferred according to the present invention have the following formula:

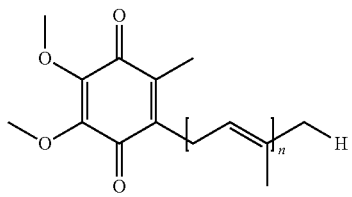

where n=6, 7, 8, 9, or 10.

Coenzyme Q-10 is most preferred in this context.

Preferred compositions according to the present invention contain purine and/or purine derivatives within narrower quantitative ranges. Cosmetic agents preferred according to the present invention are characterized here in that they contain, based on their weight, 0.001 to 2.5 wt %, by preference 0.0025 to 1 wt %, particularly preferably 0.005 to 0.5 wt %, and in particular 0.01 to 0.1 wt % purine(s) and/or purine derivative(s). Cosmetic agents preferred according to the present invention are characterized in that they contain purine, adenine, guanine, uric acid, hypoxanthine, 6-purinethiol, 6-thioguanine, xanthine, caffeine, theobromine, or theophylline. In hair-cosmetic preparations, caffeine is most preferred.

In a further preferred embodiment of the present invention the cosmetic agent contains ectoin ((S)-2-methyl-1,4,5,6-tetrahydro-4-pyrimidinecarboxylic acid).

Agents that contain, based on their weight, 0.00001 to 10.0 wt %, by preference 0.0001 to 5.0 wt %, and in particular 0.001 to 3 wt % active substances from the group constituted by carnitine, coenzyme Q-10, ectoin, a vitamin of the B series, a purine, and derivatives or physiologically acceptable salts thereof, are particularly preferred according to the present invention.

The effect of the compositions according to the present invention can be further enhanced by means of a 2-pyrrolidinone-5-carboxylic acid and derivatives thereof (J). The sodium, potassium, calcium, magnesium, or ammonium salts, in which the ammonium ion carries, beside hydrogen, one to three C$_1$ to C$_4$ alkyl groups, are preferred. The sodium salt is very particularly preferred. The quantities used in the agents according to the present invention are 0.05 to 10 wt %, based on the total agent, particularly preferably 0.1 to 5, and in particular 0.1 to 3 wt %.

The use of plant extracts as care-providing substances allows the hair treatment agents according to the present invention to be formulated in particularly near-natural fashion but nevertheless very effectively in terms of their care-providing performance. It can in fact be possible to dispense with preservatives that are otherwise usual. Preferred above all according to the present invention are the extracts from green tea, oak bark, stinging nettle, witch hazel, hops, henna, chamomile, burdock, horsetail, whitethorn, linden blossom, almond, aloe vera, pine, horse chestnut, sandalwood, juniper, coconut, mango, apricot, lemon, wheat, kiwi, melon, orange, grapefruit, sage, rosemary, birch, mallow, valerian, lady's smock, wild thyme, yarrow, thyme, melissa, restharrow, coltsfoot, hibiscus, meristem, ginseng, coffee, cocoa, moringa, ginger root, and Ayurvedic plant extracts such as, for example, *Aegle marmelos* (bilwa), *Cyperus rotundus* (nagar motha), *Emblica officinalis* (amalki), *Morida citrifolia* (ashyuka), *Tinospora cordifolia* (guduchi), *Santalum album* (chandana), *Crocus sativus* (kumkuma), *Cinnamonum zeylanicum*, and *Nelumbo nucifera* (kamala), sweet grasses such as wheat, barley, rye, oats, spelt, corn, the various types of millet (proso millet, finger millet, foxtail millet as examples), sugar cane, ryegrass, meadow foxtail, false oat-grass, bentgrass, meadow fescue, moor grass, bamboo, cottongrass, pennisetums, Andropogonodeae (*Imperata cylindrica*, also known as blood grass or cogon grass), buffalo grass, cord grass, dog's tooth grass, lovegrass, *Cymbopogon* (citronella grass), Oryzeae (rice), *Zizania* (wild rice), marram grass, blue oatgrass, soft-grasses, quaking grasses, speargrasses, couch grasses and *Echinacea*, in particular *Echinacea purpurea* (L.) Moench, all types of vine, and pericarp of *Litchi chinensis*.

The plant extracts can be used according to the present invention in both pure and dilute form. If they are used in dilute form, they usually contain approx. 2 to 80 wt % active substance and, as a solvent, the extraction agent or extraction agent mixture used to recover them.

It can occasionally be necessary to use anionic polymers. Examples of anionic monomers from which such polymers can be made are acrylic acid, methacrylic acid, crotonic acid, maleic acid anhydride, and 2-acrylamido-2-methylpropanesulfonic acid. The acid groups in this context can be present entirely or partly as a sodium, potassium, ammonium, mono- or triethanolammonium salt. Preferred monomers are 2-acrylamido-2-methylpropanesulfonic acid and acrylic acid.

Anionic polymers that contain 2-acrylamido-2-methylpropanesulfonic acid as the only monomer or co-monomer have proven to be very particularly effective, in which context the sulfonic acid group can be present entirely or partly as a sodium, potassium, ammonium, mono- or triethanolammonium salt.

The homopolymer of 2-acrylamido-2-methylpropanesulfonic acid that is obtainable commercially, for example, under the designation Rheothik® 11-80 is particularly preferred.

Preferred nonionogenic monomers are acrylamide, methacrylamide, acrylic acid esters, methacrylic acid esters, vinylpyrrolidone, vinyl ether, and vinyl esters.

Preferred anionic copolymers are acrylic acid/acrylamide copolymers as well as, in particular, polyacrylamide copolymers with sulfonic-acid-group-containing monomers. A polymer of this kind is contained in the commercial product Sepigel® 305 of the SEPPIC company.

Anionic homopolymers that are likewise preferred are uncrosslinked and crosslinked polyacrylic acids. Allyl ethers of pentaerythritol, of sucrose, and of propylene can be preferred crosslinking agents. Such compounds are obtainable commercially, for example, under the trademark Carbopol®.

Copolymers of maleic acid anhydride and methylvinyl ether, in particular those having crosslinks, are also color-preserving polymers. A maleic acid/methylvinyl ether copolymer crosslinked with 1,9-decadiene is obtainable commercially under the designation Stabileze® QM.

Anionic polymers are contained in the agents according to the present invention preferably in quantities from 0.05 to 10 wt %, based on the total agent. Quantities from 0.1 to 5 wt % are particularly preferred.

In a further embodiment, the agents according to the present invention can contain nonionogenic polymers.

Suitable nonionogenic polymers are, for example:
Vinylpyrrolidone/vinyl ester copolymers such as those marketed, for example, under the trademark Luviskol® (BASF). Luviskol® VA 64 and Luviskol® VA 73, which are each vinylpyrrolidone/vinyl acetate copolymers, are likewise preferred nonionic polymers.
Cellulose ethers such as hydroxypropyl cellulose, hydroxyethyl cellulose, and methylhydroxypropyl cellulose, such as those marketed, for example, under the trademarks Culminal® and Benecel® (AQUALON) and Natrosol® grades (Hercules). Starch and derivatives thereof, in particular starch ethers, for example Structure® XL (National Starch), a multifunctional, salt-tolerant starch,
shellac,
polyvinylpyrrolidones such as those marketed, for example, under the designation Luviskol® (BASF).

Nonionic polymers are contained in the compositions according to the present invention preferably in quantities from 0.05 to 10 wt %, based on the total agent. Quantities from 0.1 to 5 wt % are particularly preferred.

In a further embodiment, the agents according to the present invention should additionally contain at least one UV light protection filter. UVB filters can be oil-soluble or water-soluble.

The following are to be recited, for example, as oil-soluble substances:
3-benzylidene camphor, e.g. 3-(4-methylbenzylidene) camphor,
4-aminobenzoic acid derivatives, by preference 4-(dimethylamino)benzoic acid 2-ethylhexyl ester, 4-(dimethylamino)benzoic acid octyl ester, and 4-(dimethylamino)benzoic acid amyl ester,
esters of cinnamic acid, by preference 4-methoxycinnamic acid 2-ethylhexyl ester, 4-methoxycinnamic acid propyl ester, 4-methoxycinnamic acid isoamyl ester, 2-cyano-3-phenylcinnamic acid 2-ethylhexyl ester (octocrylene),
esters of salicylic acid, by preference salicylic acid 2-ethylhexyl ester, salicylic acid 4-isopropylbenzyl ester, salicylic acid homomethyl ester,
derivatives of benzophenone, by preference 2-hydroxy-4-methoxybenzophenone, 2-hydroxy-4-methoxy-4'-methylbenzophenone, 2,2'-dihydroxy-4-methoxybenzophenone,
esters of benzalmalonic acid, by preference 4-methoxybenzalmalonic acid di-2-ethylhexyl ester,
triazine derivatives such as e.g. 2,4,6-trianilino-(p-carbo-2'-ethyl-1'-hexyloxy)-1,3,5-triazine and octyltriazone,
propane-1,3-diones, such as e.g. 1-(4-tert-butylphenyl)-3-(4'-methoxyphenyl)propane-1,3-dione.

Suitable water-soluble substances are:
2-phenylbenzimidazole-5-sulfonic acid and alkali, alkaline-earth, ammonium, alkylammonium, alkanolammonium, and glucammonium salts thereof,
sulfonic acid derivatives of benzophenones, by preference 2-hydroxy-4-methoxybenzophenone-5-sulfonic acid and salts thereof,
sulfonic acid derivatives of 3-benzylidene camphor such as, for example, 4-(2-oxo-3-bornylidenemethyl)benzenesulfonic acid and 2-methyl-5-(2-oxo-3-bornylidene) sulfonic acid and salts thereof.

Typical UV-A filters that are suitable are, in particular, derivatives of benzoylmethane, for example 1-(4'-tert-butylphenyl)-3-(4'-methoxyphenyl)propane-1,3-dione or 1-phenyl-3-(4'-isopropylphenyl)propane-1,3-dione. The UV-A and UV-B filters can, of course, also be used in mixtures. In addition to the soluble substances recited, insoluble pigments are also suitable for this purpose, in particular finely dispersed metal oxides and/or salts such as e.g. titanium oxide, zinc oxide, iron oxide, aluminum oxide, cerium oxide, zirconium oxide, silicates (talc), barium sulfate, and zinc stearate. The particles should have an average diameter of less than 100 nm, by preference between 5 and 50 nm, and in particular between 15 and 30 nm. They can have a spherical shape, but those particles that possess an ellipsoidal shape or one otherwise deviating from a spherical form can also be used.

The cosmetic agents can additionally contain further active substances, adjuvants, and additives such as, for example:
structuring agents such as maleic acid and lactic acid,
swelling agents such as urea, allantoin, carbonates, or hydantoin,
dimethylisosorbide and cyclodextrins,
dyes for coloring the agent,
anti-dandruff active substances such as piroctone olamine, zinc omadine, and climbazole,
complexing agents such as EDTA, NTA, β-alaninediacetic acid, and phosphonic acids,
opacifiers such as latex, styrene/PVP and styrene/acrylamide copolymers,
luster agents such as ethylene glycol mono- and distearate as well as PEG-3 distearate,
pigments,
stabilizing agents for hydrogen peroxide and other oxidizing agents, propellants such as propane/butane mixtures, $N_2O$, dimethyl ether, $CO_2$, and air,
antioxidants
perfume oils, scents, and fragrances.

With regard to further optional components as well as the quantities of those components used, reference is made expressly to the relevant manuals known to one skilled in the art.

A further subject of the invention is therefore a method for hair treatment in which a hair treatment agent according to claim 1 is applied onto the hair and is rinsed out of the hair after a contact time.

The contact time is preferably from a few seconds to 100 minutes, particularly preferably 1 to 50 minutes, and very particularly preferably 1 to 30 minutes.

Also in accordance with the invention is a method in which a cosmetic agent according to claim 1 is applied onto the hair and remains there. "Remains on the hair" is understood according to the present invention to mean that the agent is not rinsed out of the hair again immediately after it is applied. Instead, in this case the agent remains on the hair for more than 100 minutes, until the hair is next washed.

Lastly, use of a composition as described above to reduce and/or delay dandruff on the scalp is in accordance with the invention.

The Examples below are intended to explain the subject matter of the present invention without, however, limiting it.

EXAMPLES

All quantitative indications are parts by weight unless otherwise noted. The following formulations were made available using known manufacturing methods.

Care-providing spray, also usable in foam form and/or as a hair treatment:

The pH values of all formulations were adjusted to 2 to 6.

For application as a foam, the relevant formulation is either introduced along with a propellant gas into an aerosol container, or discharged as a foam from a pump bottle using a corresponding pump attachment, for example an air foamer.

For application as a hair treatment or cream, ethylene glycol stearate and/or glycerol monostearate can additionally be added, in quantities from 0.2 to 5.0 wt %, to the formulations listed above.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition comprising, in a suitable cosmetic carrier, based in each case on the total weight of the composition:
    a) at least one selected aminofunctional silicone, in a total quantity from 0.01 to 10.0 wt %,
        wherein the aminofunctional silicone corresponds to formula (V),

| | K1 | K2 | K3 | K4 | K5 | K6 | K7 | K8 | K9 | K10 | K11 |
|---|---|---|---|---|---|---|---|---|---|---|---|
| Phenoxyethanol | 0.4 | 0.4 | 0.4 | 0.4 | 0.4 | 0.4 | 0.4 | 0.4 | 0.4 | 0.4 | 0.4 |
| Armocare VGH 70 | 0.5 | 0.5 | 0.5 | 0.5 | 0.5 | 0.5 | 0.5 | 0.5 | 0.5 | 0.5 | 0.5 |
| Titanium dioxide | 0.5 | 0.5 | — | — | — | 0.5 | 0.5 | — | — | 0.5 | 0.5 |
| Cetyl stearyl alcohol | 3.0 | 3.0 | 3.0 | 3.0 | 3.0 | 3.0 | 3.0 | 3.0 | 3.0 | 3.0 | 3.0 |
| ProSina ® | 0.5 | 0.5 | 0.5 | 0.5 | 0.5 | 0.5 | 0.5 | 0.5 | 0.5 | 0.5 | 0.5 |
| Arginine | 0.1 | — | — | — | 0.1 | — | — | 0.1 | — | — | — |
| Glutamine | — | 0.1 | — | — | — | 0.1 | — | — | — | — | — |
| Carnitine | — | — | 0.1 | — | — | — | 0.1 | 0.1 | — | — | 0.1 |
| Taurine | — | — | — | 0.1 | 0.1 | 0.1 | 0.1 | 0.1 | — | 0.1 | — |
| Laurdimonium Hydroxypropyl Hydrolyzed Keratine | 1.0 | 1.0 | 1.0 | 1.0 | 1.0 | 1.0 | 1.0 | 1.0 | 1.0 | 1.0 | 1.0 |
| Lysine | — | — | — | — | — | — | — | — | — | 0.1 | — |
| Panthenol | 0.2 | 0.2 | 0.2 | 0.2 | 0.2 | 0.2 | 0.2 | 0.2 | 0.2 | 0.2 | 0.2 |
| Soytrimonium Chloride | 1.0 | 1.0 | 1.0 | 1.0 | 1.5 | 2.5 | 5.0 | 5.0 | 5.0 | 5.0 | 5.0 |
| Ceteareth-25 | 0.3 | 0.3 | 0.3 | 0.3 | 0.3 | 0.3 | 0.3 | 0.3 | 0.3 | 0.3 | 0.3 |
| Trichogen ® VEG LS 8960 | 0.2 | 0.2 | 0.2 | 0.2 | 0.2 | 0.2 | 0.2 | 0.2 | 0.2 | 0.2 | 0.2 |
| Belsil ® ADM 8301 E | — | — | — | — | — | — | 1.0 | 1.0 | 1.0 | 1.0 | 1.0 |
| Silicone Quaternium-22 | 1.0 | 1.0 | 1.0 | 1.0 | 1.0 | 1.0 | — | — | — | — | — |
| Coco Betaine | 0.5 | 0.5 | 0.5 | 0.5 | 0.5 | 0.5 | 0.5 | 0.5 | 0.5 | 0.5 | 0.5 |
| Water, preservative, and optionally perfume oils | to 100 | to 100 | to 100 | to 100 | to 100 | to 100 | to 100 | to 100 | to 100 | to 100 | to 100 |

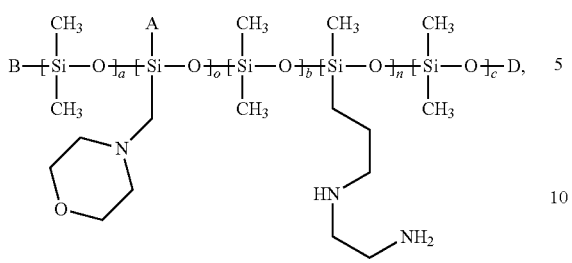

(V)

wherein

A denotes a structural unit (I), (II), or (III) bound via —O—

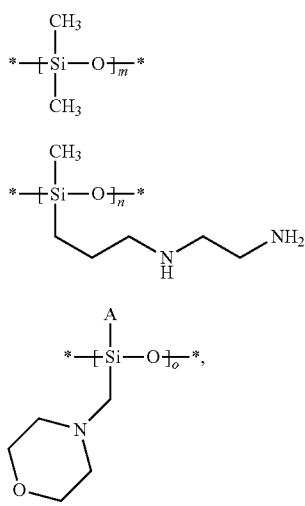

(I)

(II)

(III)

or an oligomeric or polymeric residue, bound via —O—, containing structural units of formulas (I), (II), or (III), or half of a connecting oxygen atom to a structural unit (III), or denotes —OH,

* denotes a bond to one of the structural units, (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000, and b) at least one selected cationic keratin hydrolysate, in a total quantity from 0.1 to 10.0 wt %.

2. The cosmetic composition according to claim 1, further comprising at least one quaternary ammonium compound, in a total quantity from 0.1 to 10.0 wt % based on the weight of the total composition, selected from one of the groups consisting of i) esterquats;
ii) quaternary imidazolines of formula (Tkat2),

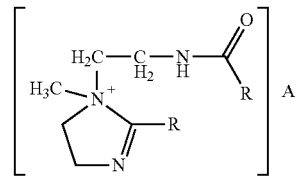

Tkat2 wherein the residues R, mutually independently in each case, denote a saturated or unsaturated, linear or branched hydrocarbon residue having a chain length from 8 to 30 carbon atoms, and A denotes a physiologically acceptable anion;

iii) amines and/or cationized amines;
iv) poly(methacryloyloxyethyltrimethylammonium) compounds;
v) quaternized cellulose derivatives, selected from the group consisting of Polyquaternium-10, Polyquaternium-24, Polyquaternium-27, Polyquaternium-67, and Polyquaternium-72;
vi) cationic alkylpolyglycosides;
vii) cationized honey;
viii) cationic guar derivatives;
ix) chitosan;
x) polymeric dimethyldiallylammonium salts and copolymers thereof with esters and amides of acrylic acid and methacrylic acid;
xi) copolymers of vinylpyrrolidone with quaternized derivatives of dialkylaminoalkyl acrylate and methacrylate;
xii) vinylpyrrolidone-vinylimidazolium methochloride copolymers;
xiii) quaternized polyvinyl alcohol;
xiv) Polyquaternium-74,
and mixtures thereof.

3. The cosmetic composition according to claim 1, wherein the cationic keratin hydrolysate corresponds to formula (I) R'—X—R"(I), wherein R' denotes a lauryl group and X denotes —N$^+$R$^{III}$$_2$R$^{IV}$— with R$^{III}$ denoting —CH$_3$ and R$^{IV}$ denoting —CH$_2$—CH(OH)—CH$_2$—, and R" denotes a hydrolysate obtained from cortex and/or cuticle of keratinic fibers.

4. The cosmetic composition according to claim 1, further comprising one or more quaternary ammonium compounds selected from the group consisting of stearamidopropyldimethylamine, distearoylethyl hydroxyethylmonium methosulfate, dicocoyl hydroxyethylmonium methosulfate, dipalmitoylethyl dimonium chloride, Quatemium-27, Quaternium-91, and behenoyl PG-trimonium chloride.

5. The cosmetic composition according to claim 1, further comprising at least one compound selected from the group consisting of a vitamin of the B series, panthenol, and calcium pantothenate.

6. The cosmetic composition according to claim 1, further comprising a zwitterionic and/or amphoteric surfactant.

7. A method for treating keratinic fibers, comprising:
applying the cosmetic composition in accordance with claim 1 onto the keratinic fibers; and
rinsing the composition out again after a contact time from a few seconds to 45 minutes.

* * * * *